US012373956B2

(12) United States Patent
Shaker et al.

(10) Patent No.: US 12,373,956 B2
(45) Date of Patent: Jul. 29, 2025

(54) SYSTEM AND METHOD FOR 3D MEDICAL IMAGE SEGMENTATION

(71) Applicant: Mohamed bin Zayed University of Artificial Intelligence, Abu Dhabi (AE)

(72) Inventors: Abdelrahman Shaker, Abu Dhabi (AE); Muhammad Maaz, Abu Dhabi (AE); Hanoona Rasheed, Abu Dhabi (AE); Salman Khan, Abu Dhabi (AE); Fahad Shahbaz Khan, Abu Dhabi (AE)

(73) Assignee: Mohamed bin Zayed University of Artificial Intelligence, Abu Dhabi (AE)

( * ) Notice: Subject to any disclaimer, the term of this patent is extended or adjusted under 35 U.S.C. 154(b) by 335 days.

(21) Appl. No.: 18/307,058

(22) Filed: Apr. 26, 2023

(65) Prior Publication Data
US 2024/0362788 A1 Oct. 31, 2024

(51) Int. Cl.
G06T 7/11 (2017.01)
G16H 30/40 (2018.01)

(52) U.S. Cl.
CPC ............ G06T 7/11 (2017.01); G16H 30/40 (2018.01); *G06T 2207/10088* (2013.01); *G06T 2207/20084* (2013.01)

(58) Field of Classification Search
CPC ............ G06T 7/11; G06T 2207/10088; G06T 2207/20084; G16H 30/40
See application file for complete search history.

(56) References Cited

U.S. PATENT DOCUMENTS

2023/0206438 A1\* 6/2023 Song .................... G06T 7/11
382/131

FOREIGN PATENT DOCUMENTS

CN 115457021 A 12/2022

OTHER PUBLICATIONS

Li et al. ; Transformer and group parallel axial attention co-encoder for medical image segmentation ; Scientific Reports ; 2022 ; 17 Pages.

(Continued)

*Primary Examiner* — David F Dunphy
(74) *Attorney, Agent, or Firm* — Oblon, McClelland, Maier & Neustadt, L.L.P.

(57) ABSTRACT

A system for 3D medical image segmentation includes a medical imaging device for obtaining a plurality of 2D images forming a volumetric image, processing circuitry, and a display. The processing circuitry is configured with a first stage to divide the volumetric image into 3D image patches, a hierarchical encoder-decoder structure in which resolution of features of the 3D image patches is decreased by a factor of two in each of a plurality of stages of the encoder, an encoder output connected to the decoder via skip connections, and a convolutional block to produce a voxel-wise final segmentation mask. The encoder includes a plurality of efficient paired attention blocks each with a spatial attention branch and a channel attention branch that learn respective spatial and channel attention feature maps. The display displays the final segmentation mask.

20 Claims, 28 Drawing Sheets

(56) References Cited

OTHER PUBLICATIONS

Liao et al. ; Swin Transformer Assisted Prior Attention Network for Medical Image Segmentation ; Applied Sciences 12 ; May 8, 2022 ; 18 Pages.
Azad et al. ; Contextual Attention Network: Transformer Meets U-Net ; Mar. 31, 2022 ; 13 Pages.
Hatamizadeh et al. ; UNETR: Transformers for 3D Medical Image Segmentation ; Oct. 9, 2021 ; 11 Pages.

* cited by examiner

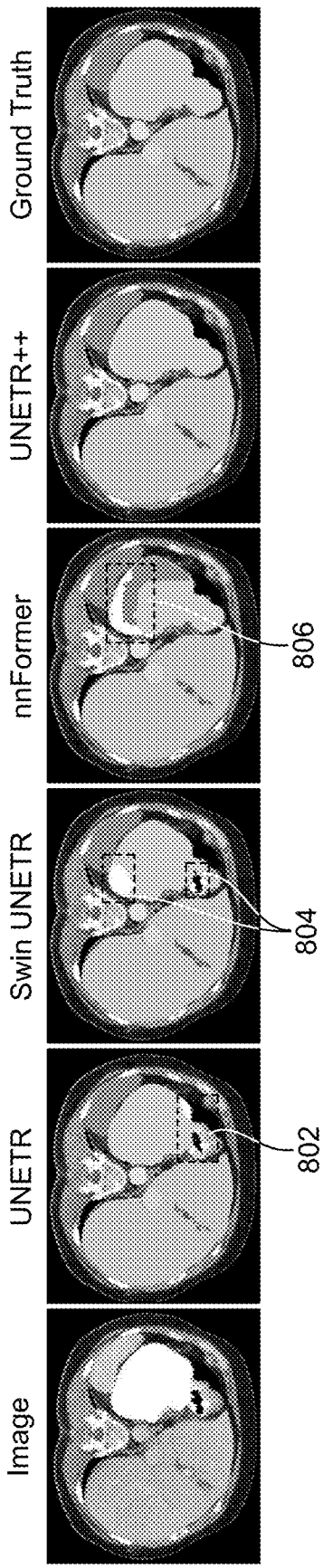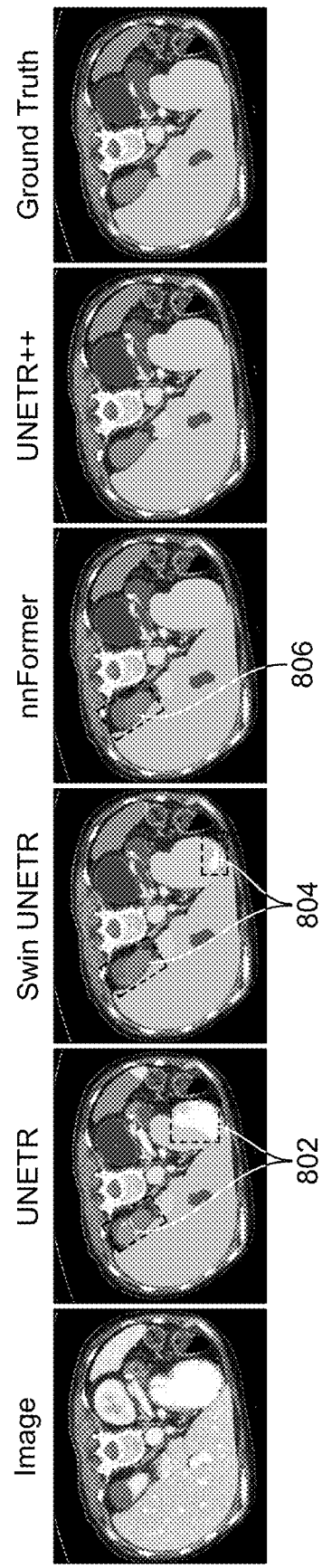
FIG. 8A
FIG. 8B

SYSTEM AND METHOD FOR 3D MEDICAL IMAGE SEGMENTATION

STATEMENT REGARDING PRIOR DISCLOSURE BY THE INVENTORS

Aspects of this technology are described in Shaker, Abdelrahman, Muhammad Maaz, Hanoona Rasheed, Salman Khan, Ming-Hsuan Yang, and Fahad Shahbaz Khan. "UNETR++: Delving into Efficient and Accurate 3D Medical Image Segmentation." arXiv preprint arXiv: 2212.04497 (2022), and is incorporated herein by reference in its entirety.

BACKGROUND

Technical Field

The present disclosure is directed to a system and method for volumetric (3D) medical image segmentation with a hybrid transformer and convolutional neural network framework that achieves both better segmentation accuracy and efficiency in terms of number of parameters and floating-point operations per second. The present disclosure provides a solution that can reduce the computational complexity for volumetric medical image reconstruction and leads to reduced cost of hardware for applications in volumetric medical image reconstruction for medical diagnosis.

Description of Related Art

Volumetric (3D) image segmentation is a fundamental technique in medical imaging with numerous applications including, tumor identification and organ localization for diagnostic purposes. See Ali Hatamizadeh, Yucheng Tang, Vishwesh Nath, Dong Yang, Andriy Myronenko, Bennett Landman, Holger R Roth, and Daguang Xu. Unetr: Transformers for 3d medical image segmentation. In Proceedings of the *IEEE/CVF Winter Conference on Applications of Computer Vision*, 2022; and Fabian Isensee, Paul F Jaeger, Simon A A Kohl, Jens Petersen, and Klaus H Maier-Hein. nnu-net: a self-configuring method for deep learning-based biomedical image segmentation. *Nature methods*, 18 (2): 203-211, 2021, each incorporated herein by reference in their entirety. Conventionally, the task of image segmentation is typically addressed by utilizing a U-Net like encoder-decoder architecture where the encoder generates a hierarchical low-dimensional representation of a 3D image and the decoder maps this learned representation to a voxel-wise segmentation. See Olaf Ronneberger, Philipp Fischer, and Thomas Brox. U-net: Convolutional networks for biomedical image segmentation. In *International Conference on Medical Image Computing and Computer-Assisted Intervention*, 2015. Earlier CNN-based methods had used convolutions and deconvolutions in the encoder and the decoder, respectively, and struggled to achieve accurate segmentation results, likely due to their limited local receptive field. On the other hand, more recent transformer-based approaches are inherently global and have demonstrated competitive performance, but at the cost of increased model complexity.

Recently, several works have explored designing hybrid architectures of CNN and transformer approaches that combine the merits of both local convolutions and global attention for volumetric segmentation. See Ali Hatamizadeh, Vishwesh Nath, Yucheng Tang, Dong Yang, Holger R Roth, and Daguang Xu. Swin unetr: Swin transformers for semantic segmentation of brain tumors in mri images. *In International MICCAI Brainlesion Workshop*, 2022; Hatamizadeh et al., *IEEE/CVF Winter Conference on Applications of Computer Vision*, 2022; and Hong-Yu Zhou, Jiansen Guo, Yinghao Zhang, Lequan Yu, Liansheng Wang, and Yizhou Yu. nnformer: Interleaved transformer for volumetric segmentation. *arXiv preprint arXiv:*2109.03201, 2021, each incorporated herein by reference in their entirety. While some hybrid approaches use transformer-based encoder with convolutional decoder, others aim at designing hybrid blocks for both encoder and decoder subnetworks. See Hatamizadeh et al., *Proceedings of the IEEE/CVF Winter Conference on Applications of Computer Vision* (2022); Hatamizadeh et al., *International MICCAI Brainlesion Workshop* (2022. However, these works mainly focus on increasing the segmentation accuracy, which in turn substantially increases the model sizes in terms of both parameters and Floating Point Operations per Second (FLOPS), leading to unsatisfactory robustness. One of the main building blocks within the transformer's architecture is the self-attention operation that models the interactions among the sequence of image patches, thereby learning global relationships. However, the self-attention mechanism is inefficient. Subsequently, the unsatisfactory robustness is primarily due to the inefficient self-attention design, which becomes even more problematic in volumetric medical image segmentation tasks, which use multiple slices. In addition, these recent approaches do not capture the explicit dependency between spatial and channel features.

CNN approaches have been applied to medical image segmentation tasks. In particular, after the introduction of the U-Net arrangement, several CNN-based approaches extended the standard U-Net architecture for various medical image segmentation tasks. See Olaf Ronneberger, Philipp Fischer, and Thomas Brox. U-net: Convolutional networks for biomedical image segmentation. In *International Conference on Medical Image Computing and Computer-Assisted Intervention*, 2015; Sijing Cai, Yunxian Tian, Harvey Lui, Haishan Zeng, YiWu, and Guannan Chen. Dense-unet: a novel multiphoton in vivo cellular image segmentation model based on a convolutional neural network. *Quantitative Imaging in Medicine and Surgery*, 10 (6): 1275, 2020; Huimin Huang, Lanfen Lin, Ruofeng Tong, Hongjie Hu, Qiaowei Zhang, Yutaro Iwamoto, Xianhua Han, Yen-Wei Chen, and JianWu. Unet 3+: A full-scale connected unet for medical image segmentation. In *IEEE International Conference on Acoustics, Speech and Signal Processing*, 2020; Zongwei Zhou, Md Mahfuzur Rahman Siddiquee, Nima Tajbakhsh, and Jianming Liang. Unet++: A nested u-net architecture for medical image segmentation. In *Deep learning in medical image analysis and multimodal learning for clinical decision support*. 2018; and Qikui Zhu, Bo Du, Baris Turkbey, Peter L Choyke, and Pingkun Yan. Deeply-supervised cnn for prostate segmentation. In *International Joint Conference on Neural Networks*, 2017, each incorporated herein by reference in their entirety. In the case of 3D medical image segmentation, the full volumetric image is typically processed as a sequence of 2D slices. See Özgün çiçek, Ahmed Abdulkadir, Soeren S Lienkamp, Thomas Brox, and Olaf Ronneberger. 3d u-net: learning dense volumetric segmentation from sparse annotation. In *International Conference on Medical Image Computing and Computer-Assisted Intervention*, 2016; Qi Dou, Hao Chen, Yueming Jin, Lequan Yu, Jing Qin, and Pheng-Ann Heng. 3d deeply supervised network for automatic liver segmentation from ct volumes. In *International Conference on Medical Image Computing and Computer-Assisted Intervention*, 2016; Eli Gibson, Francesco Giganti, Yipeng Hu, Ester Bonmati, Steve Bandula, Kurinchi Gurusamy, Brian Davidson, Stephen P Pereira, Matthew J Clarkson, and Dean C Barratt. Automatic multi-organ segmentation on abdominal ct with dense v-networks. *IEEE transactions on medical imaging*, 37 (8): 1822-1834, 2018; Fausto Milletari, Nassir Navab, and Seyed-Ahmad Ahmadi. V-net: Fully convolutional neural networks for volumetric medical image segmentation. In *Fourth International Conference on 3D Vision (3DV)*, 2016; and Jeya Maria Jose Valanarasu, Poojan Oza, Ilker Hacihaliloglu, and Vishal M Patel. Medical transformer: Gated axial-attention for medical image segmentation. In *International Conference on Medical Image Computing and Computer-Assisted Intervention*, 2021, each incorporated herein by reference in their entirety. Several works have explored hierarchical frameworks to capture contextual information. 3D representations of the volumetric image by down-sampling the volume to lower resolutions have been proposed for preserving the beneficial image features. The U-Net architecture has been extended to volumetric segmentation by replacing the 2D operations with their 3D counterparts, learning from sparsely annotated volumetric images. A generalized segmentation framework, named nnUNet, that automatically configures the architecture to extract features at multiple scales has been proposed as has a multi-scale 3D fully convolution network to learn representations from varying resolutions for multi-organ segmentation. See Holger R Roth, Hirohisa Oda, Yuichiro Hayashi, Masahiro Oda, Natsuki Shimizu, Michitaka Fujiwara, Kazunari Misawa, and Kensaku Mori. Hierarchical 3d fully convolutional networks for multi-organ segmentation. *arXiv preprint arXiv:1704.06382*, 2017, incorporated herein by reference in its entirety. Further, several efforts have been made to encode holistic contextual information within CNN-based frameworks using, e.g., image pyramids, large kernels, dilated convolution, and deformable convolution. See Hengshuang Zhao, Jianping Shi, Xiaojuan Qi, Xiaogang Wang, and Jiaya Jia. Pyramid scene parsing network. In *Proceedings of the IEEE/CVF Conference on Computer Vision and Pattern Recognition*, 2017; Chao Peng, Xiangyu Zhang, Gang Yu, Guiming Luo, and Jian Sun. Large kernel matters-improve semantic segmentation by global convolutional network. In *Proceedings of the IEEE/CVF Conference on Computer Vision and Pattern Recognition*, 2017; Liang-Chieh Chen, Yukun Zhu, George Papandreou, Florian Schroff, and Hartwig Adam. Encoder-decoder with atrous separable convolution for semantic image segmentation. In *European Conference on Computer Vision*, 2018; and Ziqiang Li, Hong Pan, Yaping Zhu, and A Kai Qin. Pgdunet: A position-guided deformable network for simultaneous segmentation of organs and tumors. In *International Joint Conference on Neural Networks*, 2020, each incorporated herein by reference in their entirety.

Transformer approaches have been applied to computer vision tasks, including medical image segmentation tasks. Vision transformers (ViTs) have recently gained popularity for machine vision tasks thanks to their ability to encode long-range dependencies. See Alexey Dosovitskiy, Lucas Beyer, Alexander Kolesnikov, Dirk Weissenborn, Xiaohua Zhai, Thomas Unterthiner, Mostafa Dehghani, Matthias Minderer, Georg Heigold, Sylvain Gelly, et al. An image is worth 16×16 words: Transformers for image recognition at scale. *arXiv preprint arXiv:2010.11929*, 2020; and Nicolas Carion, Francisco Massa, Gabriel Synnaeve, Nicolas Usunier, Alexander Kirillov, and Sergey Zagoruyko. End-to-end object detection with transformers. In *European Conference on Computer Vision*, 2020, incorporated herein by reference in its entirety. However, alleviating the complexity issue of standard self-attention operation within transformer frameworks has not been fully addressed. See Rewon Child, Scott Gray, Alec Radford, and Ilya Sutskever. Generating long sequences with sparse transformers. *arXiv preprint arXiv:1904.10509*, 2019; Nikita Kitaev, Lukasz Kaiser, and Anselm Levskaya. Reformer: The efficient transformer. In *International Conference on Learning Representations*, 2020; Muhammad Maaz, Abdelrahman Shaker, Hisham Cholakkal, Salman Khan, Syed Waqas Zamir, Rao Muhammad Anwer, and Fahad Shahbaz Khan. Edgenext: Efficiently amalgamated cnn-transformer architecture for mobile vision applications. In *International Workshop on Computational Aspects of Deep Learning at 17th European Conference on Computer Vision (CADL2022)*. Springer, 2022; and Sinong Wang, Belinda Z Li, Madian Khabsa, Han Fang, and Hao Ma. Linformer: Self-attention with linear complexity. arXiv preprint arXiv:2006.04768, 2020, each incorporated herein by reference in their entirety. However, these recent works mainly focus on the classification problem and have not studied dense prediction tasks, such as object detection in images. In the context of medical image segmentation, pure transformer designs have not been fully investigated. See Hu Cao, Yueyue Wang, Joy Chen, Dongsheng Jiang, Xiaopeng Zhang, Qi Tian, and Manning Wang. Swin-unet: Unet-like pure transformer for medical image segmentation. In *European Conference on Computer Vision Workshops*, 2022; and Davood Karimi, Serge Didenko Vasylechko, and Ali Gholipour. Convolution-free medical image segmentation using transformers. In *International Conference on Medical Image Computing and Computer-Assisted Intervention*, 2021, each incorporated herein by reference in their entirety. Dividing a volumetric image into 3D patches which are then flattened to construct a 1D embedding and passed to a backbone for global representations has been proposed. An architecture with shifted windows for 2D medical image segmentation has been introduced wherein an image is divided into patches and fed into a U-shaped encoder-decoder for local-global representation learning.

As stated earlier, other than pure CNN or transformer-based designs, several recent works have explored hybrid architectures that combine convolution and self-attention operations for better image segmentation. See Jieneng Chen, Yongyi Lu, Qihang Yu, Xiangde Luo, Ehsan Adeli, Yan Wang, Le Lu, Alan L Yuille, and Yuyin Zhou. Transunet: Transformers make strong encoders for medical image segmentation. *arXiv preprint arXiv:2102.04306*, 2021; Hatamizadeh et al, In *Proceedings of the IEEE/CVF Winter Conference on Applications of Computer Vision* (2022); Ailiang Lin, Bingzhi Chen, Jiayu Xu, Zheng Zhang, Guangming Lu, and David Zhang. Ds-transunet: Dual swin transformer u-net for medical image segmentation. *IEEE Transactions on Instrumentation and Measurement*, 2022; Valanarasu et al.; Yundong Zhang, Huiye Liu, and Qiang Hu. Transfuse: Fusing transformers and cnns for medical image segmentation. In *International Conference on Medical Image Computing and Computer-Assisted Intervention*, 2021, each incorporated herein by reference in their entirety. TransFuse proposes a parallel CNN-transformer architecture with a BiFusion module to fuse multi-level features in the encoder. MedT introduces a gated position-sensitive axial-attention mechanism in self-attention to control the positional embedding information in the encoder, while the ConvNet module in the decoder produces a segmentation model. TransUNet combines transformers and the U-Net architecture, where transformers encode the embedded image patches from convolution features and the decoder combines the upsampled encoded features with high-resolution CNN features for localization. Ds-transunet utilizes a dual-scale encoder based on Swin transformer to handle multi-scale inputs and encode local and global feature representations from different semantic scales through self-attention. See Lin et al.; and Ze Liu, Yutong Lin, Yue Cao, Han Hu, Yixuan Wei, Zheng Zhang, Stephen Lin, and Baining Guo. Swin transformer: Hierarchical vision transformer using shifted windows. In *Proceedings of the IEEE/CVF International Conference on Computer Vision,* 2021, each incorporated herein by reference in their entirety. A 3D hybrid model, UNETR, that combines the long-range spatial dependencies of a transformer with the CNN's inductive bias into a "U-shaped" encoder-decoder architecture has been introduced. The transformer blocks in UNETR are mainly used in the encoder to extract fixed global representations and then are merged at multiple resolutions with a CNN-based decoder. An approach, named nnFormer, that adapts the Swin-UNet architecture is known whereby convolution layers transform the input scans into 3D patches and volume-based self-attention modules are introduced to build hierarchical feature pyramids. However, while achieving promising performance, the computational complexity of nnFormer is significantly higher compared to UNETR and other hybrid methods.

Despite the advances in these various deep learning approaches, computer hardware for deep learning is expensive and can lead to a significant cost increase for medical imaging systems. For example, computed tomography (CT) scanners vary in speed and cost for image reconstruction. A 128 slice CT system can cost significantly more than a 16-slice CT system and can take longer sue to the larger number of slices. As mentioned above, transformer approaches for medical image reconstruction involves significant computational complexity, for example greater number of network weight parameters and more floating point operations, especially to achieve greater accuracy.

There is a need to simultaneously improve both the segmentation accuracy and the computational efficiency in a single unified framework for deep learning. The inventors have determined that capturing the explicit dependency between spatial and channel features can improve the segmentation quality. In particular, to capture a strong correlation between the spatial and channel features, the network weights for queries and keys are shared across the spatial and channel branches which also aids in controlling the number of network parameters. In addition, the network weights for values are kept independent to enforce learning complementary features in both branches.

SUMMARY

An aspect of the present disclosure is a system for 3D medical image segmentation that can include a medical imaging device for obtaining a plurality of 2D images forming a volumetric image; processing circuitry configured with a first stage to divide the volumetric image into 3D image patches, a hierarchical encoder-decoder structure in which resolution of features of the 3D image patches is decreased by a factor of two in each of a plurality of stages of the encoder, an encoder output connected to the decoder via skip connections, and a convolutional block to produce a voxel-wise final segmentation mask. The encoder includes a plurality of efficient paired attention (EPA) blocks each with a spatial attention branch and a channel attention branch that learn respective spatial and channel attention feature maps; and a display to display the final segmentation mask.

A further aspect is a method of 3D medical image segmentation that can include obtaining, by a medical imaging device, a plurality of 2D images forming a volumetric image; dividing, by a first circuitry stage, the volumetric image into 3D image patches; decreasing, in a hierarchical encoder structure, resolution of features of the 3D image patches by a factor of two in each of a plurality of stages of an encoder; transmitting an output of the encoder to a hierarchical decoder via skip connections; and learning, with spatial and channel attention branches in a plurality of efficient paired attention (EPA) blocks, spatial and channel attention feature maps; and producing, by a convolutional block, a voxel-wise final segmentation mask; and displaying on a display the final segmentation mask.

A further aspect is a non-transitory computer readable storage medium storing program instructions, which when executed by processing circuitry perform a method including obtaining a plurality of 2D images forming a volumetric image; dividing, by a first stage, the volumetric image into 3D image patches; decreasing, in a hierarchical encoder structure, resolution of features of the 3D image patches by a factor of two in each of a plurality of stages of the encoder; transmitting an output of the encoder to a hierarchical decoder via skip connections; and learning, with spatial and channel attention branches in a plurality of efficient paired attention (EPA) blocks, spatial and channel attention feature maps; producing, by a convolutional block, a voxel-wise final segmentation mask; and displaying on a display the final segmentation mask.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 8A, 8B, 8C illustrate a qualitative comparison of the UNETR++ network with conventional approaches on abdominal multi-organ segmentation;

DETAILED DESCRIPTION

Figure 1:
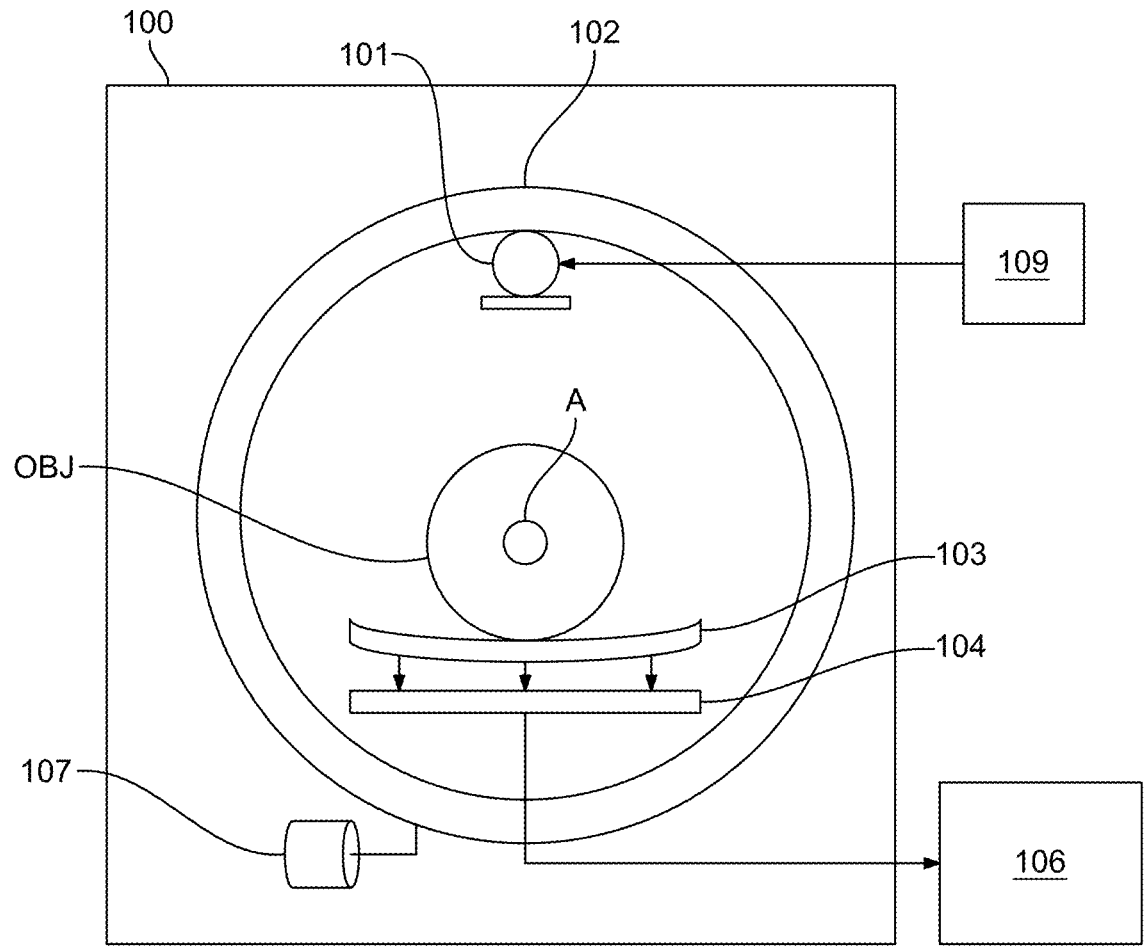
FIG. 1 is a schematic of an implementation of a typical computed tomography (CT) scanner.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Medical 3D image segmentation is an important image processing step in medical image analysis. Segmentation methods with high precision (including high reproducibility) and low bias are a main goal in surgical planning because they directly impact the results, for example, the detection and monitoring of tumor progress. Accurately recognizing a change in subject patterns and/or symptoms is of great value for early diagnosis and efficient monitoring of diseases. Medical 3D image segmentation is typically performed using computerized tomography (CT) and magnetic resonance imaging (MRI). Another volumetric imaging technique is Digital breast tomosynthesis (DBT). DBT is an imaging technique that allows a volumetric reconstruction of the whole breast from a finite number of low-dose two-dimensional projections obtained by different X-ray tube angles.

On the other hand, the hardware cost for medical 3D image reconstruction increases significantly with the number of slices, as does the cost of 3D medical image segmentation. The cost of 3D medical image segmentation significantly increases due to the increased number of network weight parameters and floating point operations required for deep learning-based image segmentation across multiple slices. Subsequently, there is a need to improve 3D medical image segmentation accuracy but reduce computational complexity in order to minimize computer hardware costs for medical imaging systems. The present deep learning framework achieves an improvement in computational complexity by reducing the model complexity by about 70 percent over conventional deep learning approaches in terms of the number of parameters and reduction in number of floating point operations. An example implementation of the present invention was made using a single Nvidia A100 GPU with 40 GB of video RAM. In contrast, a conventional approach, referred to as UNETR was implemented using an Nvidia DGX-1 which is equipped with e GPUs with 128 GB of total HBM2 memory.

The Dice coefficient (DICE), also called the overlap index, is a widely used metric in validating medical volume segmentations. The DICE is a direct comparison between automatic and ground truth image segmentations.

As discussed above, most hybrid deep learning approaches, such as UNETR and nnFormer, have achieved improved segmentation accuracy compared to their pure CNNs and transformer-based counterparts. See Ali Hatamizadeh, et al., In Proceedings of the IEEE/CVF Winter Conference on Applications of Computer Vision (2022). However, this pursuit of increasing the segmentation accuracy by these hybrid approaches comes at the cost of substantially more complex models (both in terms of number of network weight parameters and floating point operations (FLOPs)), which can also lead to unsatisfactory robustness. For instance, UNETR achieves favorable accuracy but comprises 2.5 times more parameters, compared to the best conventional CNN-based nnUNet. Moreover, nnFormer obtains improved performance over UNETR but further increases the number of parameters by 1.6 times and FLOPs by 2.8 times. Furthermore, these aforementioned hybrid deep learning approaches struggle to effectively capture the interdependencies between feature channels to obtain an enriched feature representation that encodes both the spatial information as well as the inter-channel feature dependencies.

The present disclosure provides an efficient hybrid hierarchical architecture for medical 3D image segmentation, named the UNETR++ network, that achieves both better segmentation accuracy and efficiency in terms of number of parameters and FLOPs. The UNETR++ network is a hierarchical approach that incorporates efficient paired attention (EPA) blocks that efficiently capture enriched inter-dependent spatial and channel features by applying both spatial and channel attention in two respective branches. The spatial attention in EPA projects the keys and values to a fixed lower dimensional space, making the self-attention computation linear with respect to the number of input tokens. In addition, the channel attention emphasizes the dependencies between the channel feature maps by performing the dot-product operation between queries and keys in the channel dimension. Further, to capture a strong correlation between the spatial and channel features, the weights for queries and keys are shared across the two branches which also aids in controlling the number of network parameters. Still further, the weights for values are kept independent to enforce learning complementary features in both branches.

A computerized tomography (CT) scan combines a series of X-ray images taken from different angles around a patient's body and uses computer processing to create cross-sectional images (slices) of the bones, blood vessels and soft tissues inside the body. A CT scan is produced using a CT scanner. A CT scanner is typically a large, donut-shaped machine with a short tunnel in the center. The patient will lie on a narrow table that slides in and out of this short tunnel. Rotating around the patient, the x-ray tube and electronic x-ray detectors are located opposite each other in a ring, called a gantry. A computer workstation that processes the imaging information is in a separate control room. This is where the technologist operates the scanner and monitors the exam in direct visual contact. The technologist may hear and talk to the patient using a speaker and microphone.

With CT scanning, several x-ray beams and electronic x-ray detectors rotate around the patient. These measure the amount of radiation being absorbed throughout the patient's body. Sometimes, the exam table will move during the scan. A special computer program processes this large volume of data to create two-dimensional cross-sectional images of the patient's body. The system displays the images on a computer monitor. CT imaging is sometimes compared to looking into a loaf of bread by cutting the loaf into thin slices. When the computer software reassembles the image slices, the result is a very detailed multidimensional view of the body's interior.

FIG. 1 is a schematic of an example computed tomography (CT) scanner. As shown in FIG. 1, a radiography gantry 100 includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis A. A rotating unit 107 rotates the annular frame 102 at a high speed, while the object OBJ is being moved along the axis A into or out of the page.

The CT apparatus further includes a high voltage generator 109 that generates a tube voltage applied to the X-ray tube 101 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that have transmitted through the object OBJ. The X-ray detector 103 further includes individual detector elements or units.

The CT apparatus further includes other devices for processing the detected signals from X-ray detector 103. A data acquisition circuit or a Data Acquisition System (DAS) 104 converts a signal output from the X-ray detector 103 into a voltage signal, amplifies the signal, and further converts the signal into a digital signal. The X-ray detector 103 and the DAS 104 are configured to handle a predetermined total number of projections per rotation.

The above-described data is sent to a processing device 106 which includes a memory, reconstruction processing circuitry and a display. The memory stores the resultant data, which is also called projection data, at a stage immediately before reconstruction by the processing circuitry. The memory can store the measurement value representative of the irradiance of the X-rays at the X-ray detector unit 103. Further, the memory can store a dedicated program for executing various steps of method for CT image reconstruction by the reconstruction device.

The reconstruction device can execute CT image reconstruction. Further, reconstruction device can execute pre-reconstruction processing image processing such as volume rendering processing and image difference processing as needed. The reconstruction device can use the memory to store, e.g., projection data, reconstructed images, calibration data and parameters, and computer programs. In one implementation, the reconstructed images can be displayed on a display.

Magnetic resonance imaging (MRI) is a medical imaging technique that uses a magnetic field and computer-generated radio waves to create detailed images of the organs and tissues in a patient's body. Unlike a CT scan, it does not use x-rays or other radiation. An MRI system also includes image reconstruction processing circuitry.

Figure 2:
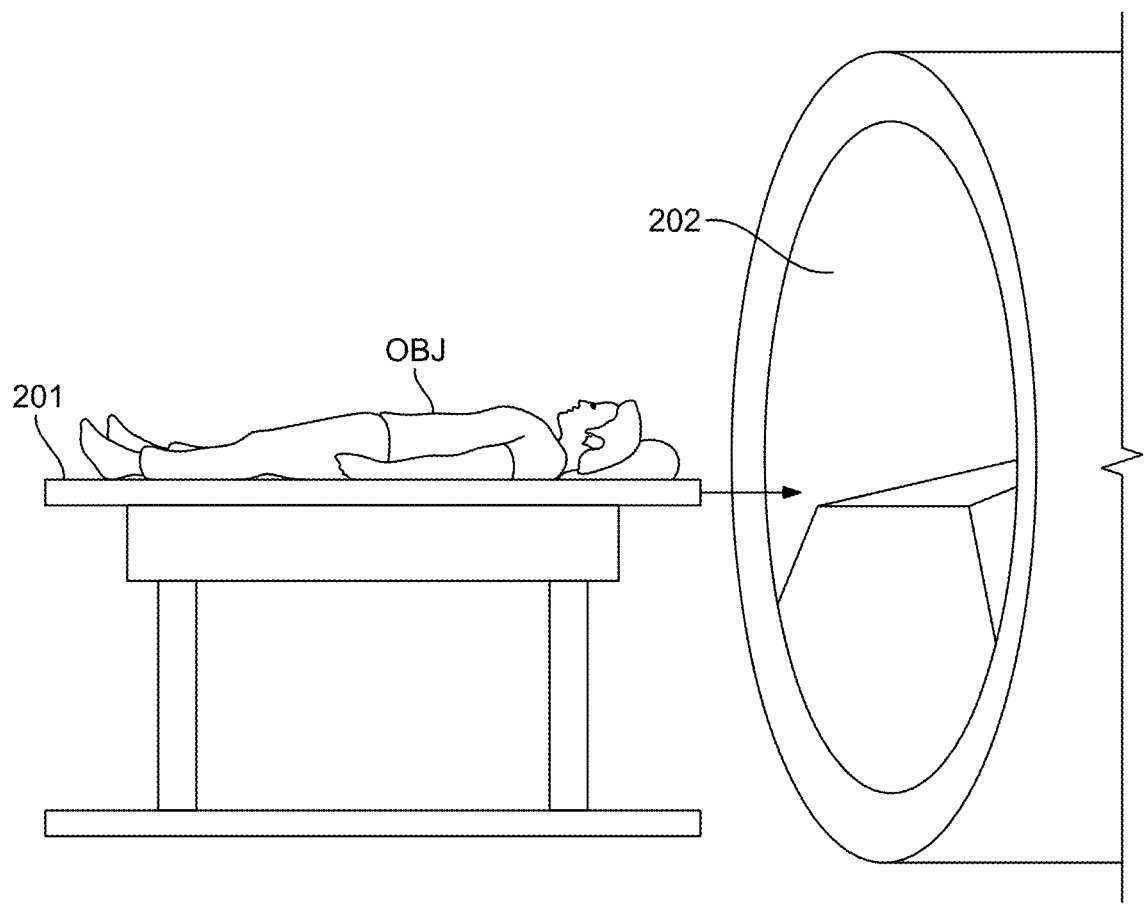
FIG. 2 is a schematic of an implementation of a typical magnetic resonance imaging (MRI)

FIG. 2 is a schematic of an implementation of a typical magnetic resonance imaging (MRI). MRI imaging is performed using an MRI machine 202. An MRI machine uses a powerful magnet to make cross-sectional images of a patient's body. The MRI machine can also produce 3D images that can be viewed from different angles. Most MRI machines are large, tube-shaped magnets. When the patient OBJ lies on a table 201 that is moved to inside an MRI machine 202, the magnetic field temporarily realigns water molecules in the body. Radio waves cause these aligned atoms to produce faint signals, which are used to create the cross-sectional MRI images.

The present disclosure is directed to an efficient hybrid hierarchical architecture for use in a system and/or method for 3D medical image segmentation of 3D medical images from CT scans and MRI images.

Conventional hybrid methods that combine transformer and CNN techniques employ a self-attention operation of the transformer. The self-attention operation has a quadratic complexity in terms of the number of tokens. Subsequently, the self-attention operation is computationally expensive, especially in the case of volumetric medical segmentation which involves a series of stacked 2D images. The self-attention operation can be especially computationally expensive in the case of interleaving window attention and convolution components in hybrid designs, as sliding windows have a degree of overlap between windows.

In a transformer, a self-attention layer contextually encodes the input information. Self-attention compares all input members with each other, and modifies the corresponding output positions. In other words, self-attention layer differentially key-value searches the input for each input, and adds results to the output. Subsequentially, the computational complexity is quadratic in input length ($O(L^2)$) to calculate an L×L attention matrix.

Different from conventional hybrid methods, the present hybrid framework employs self-attention across feature channels instead of in a volume dimension. The present hybrid framework reduces the computational complexity from quadratic to linear compared to the volumetric dimension. Further, the spatial attention information can be efficiently learned by projecting the spatial matrices of the keys and values into a lower-dimension space.

Conventional hybrid volumetric medical image segmentation approaches typically capture the spatial features through an attention computation and ignore the channel information in the form of encoding the inter-dependencies between different channel feature maps. In contrast, effectively combining the interactions in the spatial dimensions and the inter-dependencies between the channel features provides enriched contextual spatial-channel feature representations, leading to improved mask predictions.

Overall Architecture

Figure 3A:
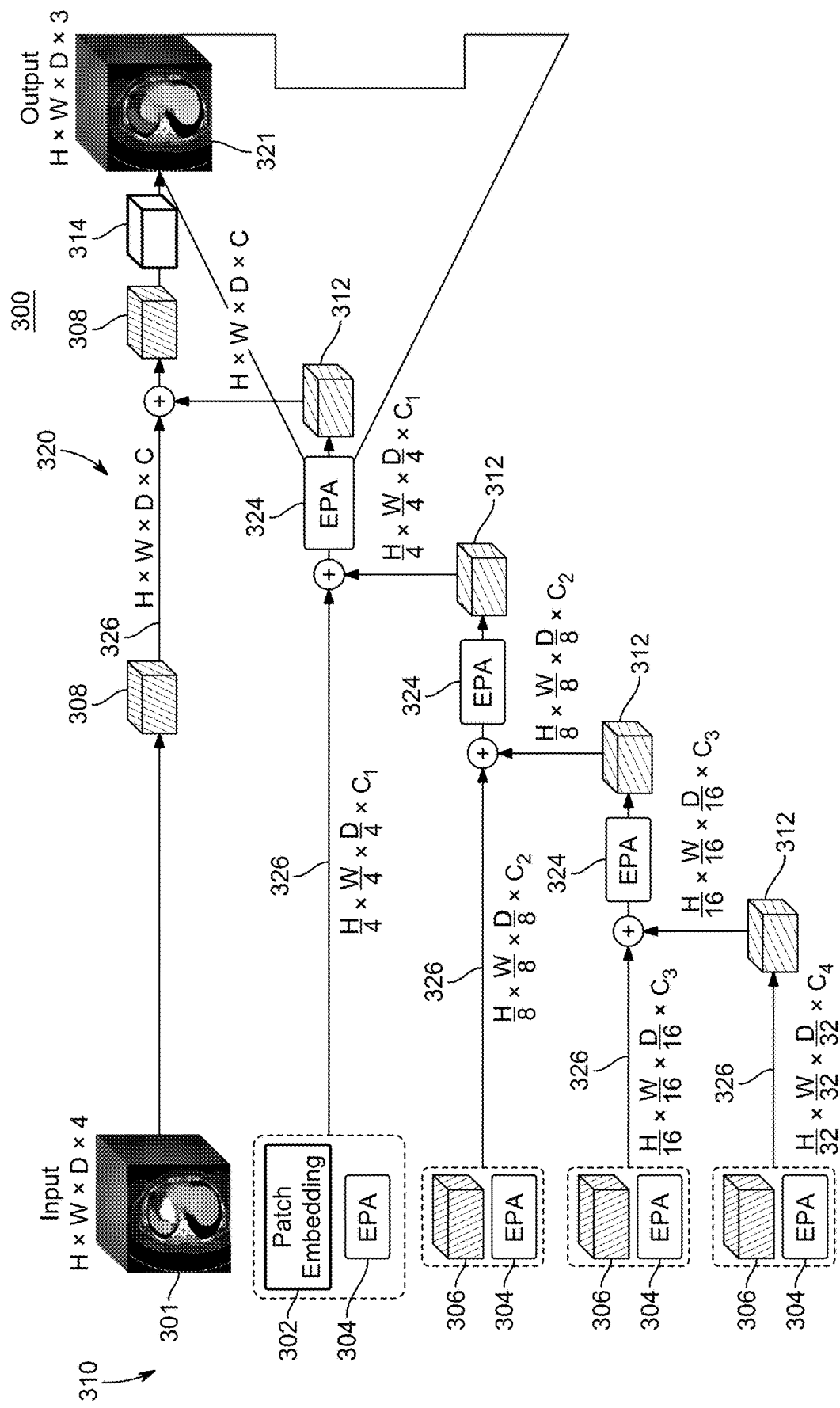
FIG. 3A is a hierarchical encoder-decoder deep neural network structure, in accordance with an exemplary aspect of the disclosure.

FIG. 3A is a hierarchical encoder-decoder deep neural network structure, in accordance with an exemplary aspect of the disclosure. The UNETR++ framework 300 includes skip connections 326 between the encoders 310 and decoders 320, followed by convolutional blocks (ConvBlocks 308) to generate the prediction masks. Instead of using a fixed feature resolution throughout the encoders 310, the UNETR++ framework employs a hierarchical design where the resolution of the features is gradually decreased by a factor of two in each stage. Within the UNETR++ framework, the encoder 310 has four stages, where the first stage consists of patch embedding 302 to divide volumetric input into 3D patches, followed by an efficient paired-attention (EPA) block 304. In the patch embedding 302, each 3D input (volume) $x \in \mathbb{R}^{H \times W \times D}$ is divided into non-overlapping patches $x_u \in \mathbb{R}^{N \times (P_1, P_2, P_3)}$, where $(P_1, P_2, P_3)$ is the resolution of each patch and $$N = \left( \frac{H}{P_1} \times \frac{W}{P_2} \times \frac{D}{P_3} \right)$$

denotes the length of the sequence. Then, the patches are projected into C channel dimensions, producing feature maps of size $$\frac{H}{P_1} \times \frac{W}{P_2} \times \frac{D}{P_3} \times C.$$

The framework uses the same patch resolution (4, 4, 2), as in Zhou et al. Yizhou Yu. nnformer: Interleaved transformer for volumetric segmentation. *arXiv preprint arXiv: 2109.03201*, 2021, incorporated herein by reference. For each of the remaining encoder stages, downsampling layers 306 are employed using non-overlapping convolution to decrease the resolution by a factor of two, followed by the EPA block 304.

Within the UNETR++ framework, each EPA block comprises two attention modules to efficiently learn enriched spatial-channel feature representations by encoding the information in both spatial and channel dimensions with a shared keys-queries scheme, i.e., shared weights for keys and shared weights for queries.

The encoder stages are connected with the decoder stages via skip connections 326 to merge the outputs at the respective different resolutions. This enables the recovery of the spatial information lost during the downsampling operations, leading to predicting a more precise output. Similar to the encoder, the decoder 320 also comprises four stages, where each decoder stage consists of an upsampling layer 312 using deconvolution to increase the resolution of the feature maps by a factor of two, followed by the EPA block 324 (except the last decoder). The number of channels is decreased by a factor of two between two decoder stages. Consequently, the outputs of the last decoder are fused with convolutional feature maps to recover the spatial information and enhance the feature representation. The resulting output is then fed into 3×3×3 and 1×1×1 convolutional blocks 314 to generate voxel-wise final mask predictions 321.

The deconvolutional layers increase the resolution of the feature maps by a factor of two. However, a 3×3×3 convolutional block is used at the last stage to compensate the heavy self-attention computation because the spatial size at this stage will be significantly larger (i.e. [128, 128, 64, 16] in the case of Synapse dataset). The output of the last decoder stage is fused with convolutional features to recover the spatial information and enhance the feature representation.

In an example implementation, the architecture for UNETR++ consists of a hierarchical encoder-decoder structure. The encoder has four stages in which the number of channels at stages $[C_1, C_2, C_3, C_4]$ are [32, 64, 128, 256] and each stage has three EPA blocks with the number of heads set to four. Similarly, the decoder has four stages, each consisting of upsampling using deconvolution followed by three EPA blocks.

Figure 3B:
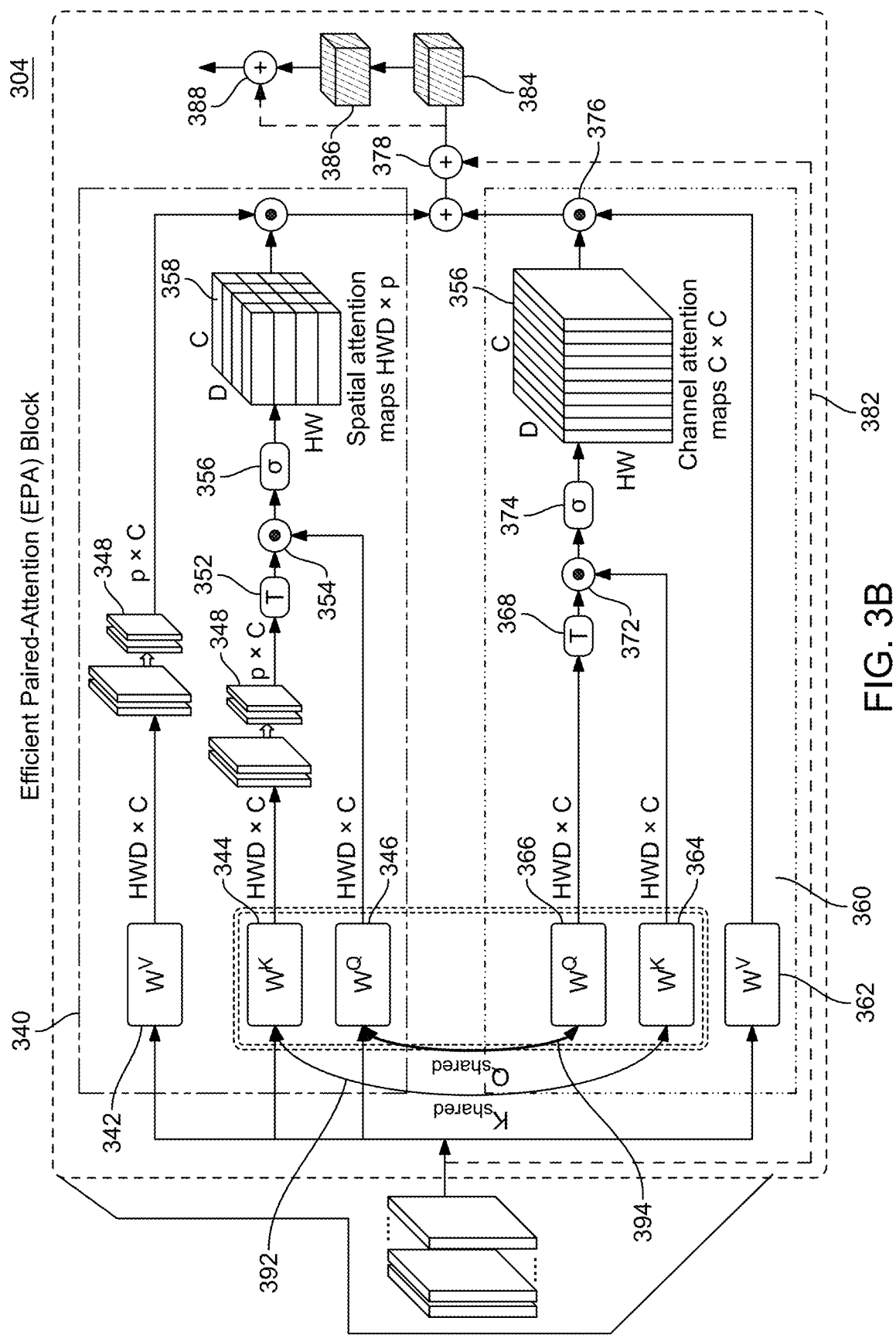
FIG. 3B is a structure for an efficient paired-attention (EPA) block of the deep neural network structure.

FIG. 3B is a structure for an efficient paired-attention (EPA) block of the deep neural network structure. Each EPA block performs two tasks using parallel attention modules with shared keys-queries and different value layers to efficiently learn enriched spatial-channel feature representations. As illustrated in FIG. 3B, the first attention module 340 aggregates the spatial features by a weighted sum of the projected features in a linear manner to compute the spatial attention maps 358, while the second attention module 360 emphasizes the dependencies in the channels and computes the channel attention maps 356.

The EPA block 304 performs efficient global attention and effectively captures enriched spatial-channel feature representations. The EPA block 304 comprises spatial attention 340 and channel attention 360 modules. The spatial attention module 340 reduces the complexity of the self-attention from quadratic to linear. In addition, the channel attention 360 module effectively learns the inter-dependencies between the channel feature maps. The EPA block 304 is based on a shared key weight query weight scheme between the two attention modules 340, 360 to be mutually informed in order to generate better and more efficient feature representation. This improved feature representation is due to learning complementary features by sharing the key weights and query weights but using different value layers.

As illustrated in FIG. 3B, the generated feature maps by the patch embedding x of size $$\frac{H}{4} \times \frac{W}{4} \times \frac{D}{2} \times C$$

are fed directly into consecutive EPA blocks 304 followed by three encoder stages. The weights of Q and K linear layers are shared across the two attention modules and a different V layer is used for each attention module. The two attention modules are computed as:

$$\hat{X}_s = SA(Q_{shared}, K_{shared}, V_{spatial}), \quad (1)$$

$$\hat{X}_c = CA(Q_{shared}, K_{shared}, V_{channel}), \quad (2)$$

where, $\hat{X}_s$ and $\hat{X}_c$ denotes the spatial 340 and channels 360 attention maps, respectively. SA is the spatial attention 340 module, and CA is the channel attention 360 module.

$Q_{shared}$, $K_{shared}$, and $V_{channel}$ are the matrices for shared queries, shared keys, spatial value layer, and channel value layer, respectively.

Spatial Attention 340: the spatial information is efficiently learned by reducing the complexity from $O(n^2)$ to $O(np)$, where n is the number of tokens, and p is the dimension of the projected vector, where p<<n. Given a normalized tensor X of shape HW D×C, $Q_{shared}$, $K_{shared}$, and $V_{spatial}$ projections are computed using three linear layers, yielding $Q_{shared}=W^Q X$, $K_{shared}=W^K X$, and $V_{spatial}=W^V X$, with dimensions HWD×C, where $W^Q$ 346, $W^K$ 344, and $W^V$ 342 are the projection weights for $Q_{shared}$, $K_{shared}$, and $V_{spatial}$, respectively. Then, three steps are performed.

First, the $K_{shared}$ and $V_{spatial}$ layers are projected from HWD×C into lower-dimensional matrices 348 of shape p×C. As noted above, it has been determined that the spatial attention information can be efficiently learned by projecting values $V_{spatial}$ and keys $K_{shared}$ into lower-dimension space p×C.

Second, the spatial attention maps 358 are computed by multiplying 354 the $Q_{shared}$ layer 394 by the transpose 352 of the projected $K_{shared}$ 392, followed by softmax 356 to measure the similarity between each feature Q and the rest of the spatial features K.

Third, these similarities are multiplied by the projected $V_{spatial}$ layer 348 to produce the final spatial attention maps 358 of shape HWD×C. The spatial attention 358 is defined as follows:

$$\hat{X}_p = Softmax\left(\frac{Q_{shared}K_{proj}^T}{\sqrt{d}}\right) \cdot \hat{V}_{spatial}, \quad (3)$$

where, $Q_{shared}$, $K_{proj}$, $\hat{V}_{spatial}$ denote shared queries, projected shared keys, and projected spatial value layer, respectively, and d is the size of each vector.

Channel Attention 360: The channel attention module captures the interdependencies between feature channels by applying the dot-product operation 376 in the channel dimension between channel value layer 362 and channel attention maps 356. Using the same $Q_{shared}$ 394 and $K_{shared}$ 392 of the spatial attention module 340, the value layer is computed for the channels to learn the complementary features using linear layer, yielding $V_{channel}=W^V X$, with dimensions HWD×C, where WY is the projection weight for $V_{channel}$. The channel attention 360 is defined as follows:

$$\hat{X}_c = V_{channel} \cdot Softmax\left(\frac{Q_{shared}^T K_{shared}}{\sqrt{d}}\right), \quad (4)$$

where, $V_{channel}$, $Q_{shared}$, $K_{shared}$ denote channel value layer 362, shared queries 366, and shared keys 364, respectively, and d is the size of each vector.

Finally, sum fusion 378 and transform the outputs from the two attention modules 340, 360 are performed by convolution blocks 384, 386 to obtain enriched feature representations. The final output $\hat{X}$ of the EPA block 304 is obtained as:

$$\hat{X} = Conv_1(Conv_3(\hat{X}_s + \hat{X}_c)), \quad (5)$$

where, $\hat{X}_s$ and $\hat{X}_c$ denotes the spatial and channels attention maps, and $Conv_1$ 386 and $Conv_3$ 384 are 1×1×1 and 3×3×3 convolution blocks, respectively.

Loss Function

A loss function is used in training that is based on a summation of the commonly used soft dice loss and cross-entropy loss to simultaneously leverage the benefits of both complementary loss functions. It is defined as:

$$\mathcal{L}(Y, P) = 1 - \sum_{i=1}^{I}\left(\frac{2*\sum_{v=1}^{V} Y_{v,i} \cdot P_{v,i}}{\sum_{v=1}^{V} Y_{v,i}^2 + \sum_{v=1}^{V} P_{v,i}^2} + \sum_{v=1}^{V} Y_{v,i} \log P_{v,i}\right), \quad (6)$$

where, I denotes the number of classes;
V denotes the number of voxels;
$Y_{v,i}$ and $P_{v,i}$ denote the ground truths and output probabilities at voxel v for class i, respectively.

For the Synapse dataset, all the models are trained for 1K epochs with inputs of size 128×128×64. For BTCV, the same training recipe is followed as in Hatamizadeh et al. and train all the models at 96×96×96 resolution for 5K epochs. For ACDC, Decathlon-Lung, and BRaTs, all the models are trained at 160×160×16 resolution. All other training hyper-parameters are the same as in Zhou et al. (2021). Further, learnable positional encodings are added to the input of each EPA block.

Experiments

The UNETR++ approach is validated by conducting comprehensive experiments on five benchmarks: Synapse for multi-organ CT segmentation, BTCV for multi-organ CT segmentation, ACDC for Automated Cardiac Diagnosis, Brain Tumor Segmentation (BRaTs), and Medical Segmentation Decathlon-Lung. See Bennett Landman, Zhoubing Xu, J Igelsias, Martin Styner, T Langerak, and Arno Klein. Miccai multi-atlas labeling beyond the cranial vault-workshop and challenge. In *MIC-CAI Multi-Atlas Labeling Beyond Cranial Vault—Workshop Challenge*, 2015; Olivier Bernard, Alain Lalande, Clement Zotti, Frederick Cervenansky, Xin Yang, Pheng-Ann Heng, Irem Cetin, Karim Lekadir, Oscar Camara, Miguel Angel Gonzalez Ballester, Gerard Sanroma, Sandy Napel, Steffen Petersen, Georgios Tziritas, Elias Grinias, Mahendra Khened, Varghese Alex Kollerathu, Ganapathy Krishnamurthi, Marc-Michel Roh'e, Xavier Pennec, Maxime Sermesant, Fabian Isensee, Paul J"ager, Klaus H. Maier-Hein, Peter M. Full, Ivo Wolf, Sandy Engelhardt, Christian F. Baumgartner, Lisa M. Koch, Jelmer M. Wolterink, Ivana I'sgum, Yeonggul Jang, Yoonmi Hong, Jay Patravali, Shubham Jain, Olivier Humbert, and Pierre-Marc Jodoin. Deep learning techniques for automatic mri cardiac multi-structures segmentation and diagnosis: Is the problem solved? *IEEE Transactions on Medical Imaging*, 37 (11): 2514-2525, 2018; Bjoern H. Menze, Andras Jakab, Stefan Bauer, Jayashree Kalpathy-Cramer, Keyvan Farahani, Justin Kirby, Yuliya Burren, Nicole Porz, Johannes Slotboom, Roland Wiest, Levente Lanczi, Elizabeth Gerstner, Marc-André Weber, Tal Arbel, Brian B. Avants, Nicholas Ayache, Patricia Buendia, D. Louis Collins, Nicolas Cordier, Jason J. Corso, Antonio Criminisi, Tilak Das, Hervé Delingette, C, ag˘ atay Demiralp, Christopher R. Durst, Michel Dojat, Senan Doyle, Joana Festa, Florence Forbes, Ezequiel Geremia, Ben Glocker, Polina Golland, Xiaotao Guo, Andac Hamamci, Khan M. Iftekharuddin, Raj Jena, Nigel M. John, Ender Konukoglu, Danial Lashkari, Jose' Antonio Mariz, Raphael Meier, Se'rgio Pereira, Doina Precup, Stephen J. Price, Tammy Riklin Raviv, Syed M. S. Reza, Michael Ryan, Duygu Sarikaya, Lawrence Schwartz, Hoo-Chang Shin, Jamie Shotton, Carlos A. Silva, Nuno Sousa, Nagesh K. Subbanna, Gabor Szekely, Thomas J. Taylor, Owen M. Thomas, Nicholas J. Tustison, Gozde Unal, Flor Vasseur, Max Wintermark, Dong Hye Ye, Liang Zhao, Binsheng Zhao, Darko Zikic, Marcel Prastawa, Mauricio Reyes, and Koen Van Leemput. The multimodal brain tumor image segmentation benchmark (brats). *IEEE Transactions on Medical Imaging*, 34 (10): 1993-2024, 2015; Amber L. Simpson, Michela Antonelli, Spyridon Bakas, Michel Bilello, Keyvan Farahani, Bram van Ginneken, Annette Kopp-Schneider, Bennett A. Landman, Geert Litjens, Bjoern Menze, Olaf Ronneberger, Ronald M. Summers, Patrick Bilic, Patrick F. Christ, Richard K. G. Do, Marc Gollub, Jennifer Golia-Pernicka, Stephan H. Heckers, William R. Jarnagin, Maureen K. McHugo, Sandy Napel, Eugene Vorontsov, Lena Maier-Hein, and M. Jorge Cardoso. A large annotated medical image dataset for the development and evaluation of segmentation algorithms, 2019, each incorporated herein by reference in their entirety. Both qualitative and quantitative results demonstrate the effectiveness of the UNETR++ framework, leading to better performance in terms of segmentation accuracy and model efficiency compared to the existing methods in the literature.

For purposes of evaluation, a comparison is made with the UNETR network. An overview of the model architecture is presented in FIG. 4. UNETR 400 utilizes a contracting-expanding pattern consisting of a stack of transformers as the encoder 410 which is connected to a decoder 420 via skip connections 430. A 1D sequence of a 3D input volume $x \in \mathbb{R}^{H \times W \times D \times C}$ created with resolution (H,W,D) and C input channels by dividing it into flattened uniform non-overlapping patches 402 $x_v \in \mathbb{R}^{N \times (P^3 \cdot C)}$ where (P, P, P) denotes the resolution of each patch and N=(H×W×D)/$P^3$ is the length of the sequence.

Subsequently, a linear layer 404 is used to project the patches 402 into a K dimensional embedding space 406, which remains constant throughout the transformer layers. In order to preserve the spatial information of the extracted patches, a 1D learnable positional embedding $E_{pos} \in \mathbb{R}^{N \times K}$ is added to the projected patch embedding $E \in \mathbb{R}^{(P^3 \cdot C) \times K}$ according to $$Z_0 = [x_v^1 E; x_v^2 E; \ldots; x_v^N E] + E_{pos},$$

Note that the learnable [class] token is not added to the sequence of embeddings since the transformer backbone is designed for semantic segmentation. After the embedding layer 406, a stack of transformer blocks 410 is utilized comprising of multi-head self-attention (MSA 412) and multilayer perceptron (MLP 414) sublayers according to $$z_i' = MSA(Norm(z_{i-1})) + z_{i-1}, i = 1 \ldots L,$$
$$z_i = MLP(Norm(z'i)) + z'i, i = 1 \ldots L,$$

where Norm ( ) denotes layer normalization, MLP comprises of two linear layers with GELU activation functions, i is the intermediate block identifier, and L is the number of transformer layers.

A MSA sublayer 412 comprises of n parallel self-attention (SA) heads. Specifically, the SA block, is a parameterized function that learns the mapping between a query (q) and the corresponding key (k) and value (v) representations in a sequence $z \in \mathbb{R}^{N \times K}$. The attention weights (A) are computed by measuring the similarity between two elements in z and their key-value pairs according to $$A = Softmax\left(\frac{qk^T}{\sqrt{K_h}}\right),$$

where $K_h$=K/n is a scaling factor for maintaining the number of parameters to a constant value with different values of the key k. Using the computed attention weights, the output of SA for values v in the sequence z is computed as $$SA(z) = Av,$$

Here, v denotes the values in the input sequence and $K_h$=K/n is a scaling factor. Furthermore, the output of MSA is defined as $$MSA(z) = [SA_1(z); SA_2(z); \ldots; SA_n(z)]W_{msa},$$

where $W_{msa} \in \mathbb{R}^{nK_h \times K}$ represents the multi-headed trainable parameter weights.

Inspired by architectures that are similar to U-Net, where features from multiple resolutions of the encoder are merged with the decoder, a sequence representation 432, $z_i$ (i∈{3, 6,9,12}), is extracted with size $$\frac{H \times W \times D}{P^3} \times K,$$

from the transformer and reshape 424 (e.g., with a 2×2×2 deconvolution layer, a 3×3×3 convolution layer, batch normalization (BN), and rectified linear unit (ReLU)) them into a $$\frac{H}{P} \times \frac{W}{P} \times \frac{D}{P} \times K$$

tensor 434.

Figure 4:
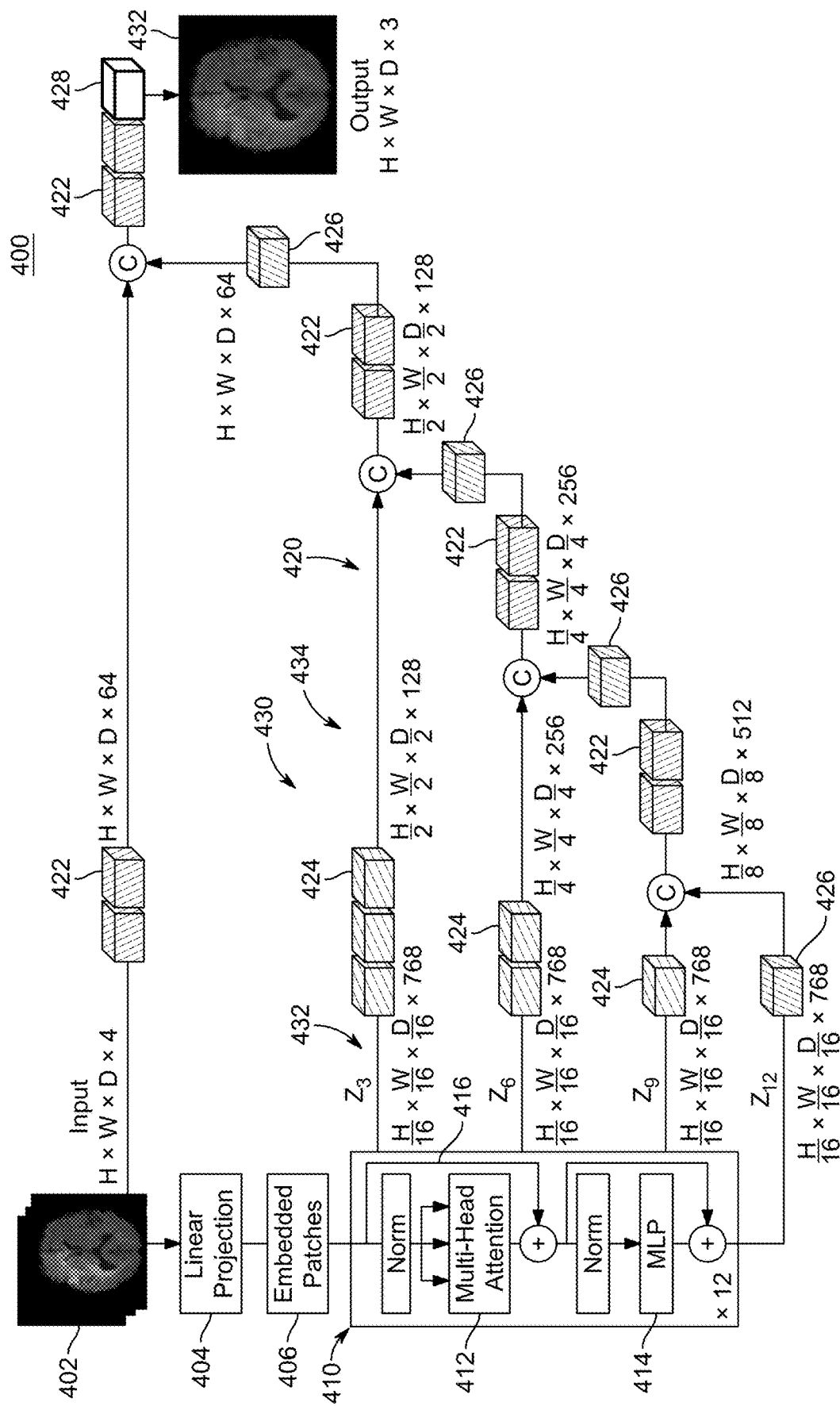
FIG. 4 is an architecture of a UNEt TRansformer (UN-ETR network)

A representation in the definition is in the embedding space after it has been reshaped as an output of the transformer with feature size of K (i.e. transformer's embedding size). Furthermore, as shown in FIG. 4, at each resolution the reshaped tensors are projected from the embedding space into the input space by utilizing consecutive 3×3×3 convolutional layers that are followed by normalization layers.

At the bottleneck of the encoder (i.e. output of transformer's 410 last layer), a deconvolutional layer 426 (e.g., a 2×2×2 layer) is applied to the transformed feature map to increase its resolution by a factor of 2. The resized feature map is concatenated with the feature map of the previous transformer output (e.g. z9), and feed them into consecutive 3×3×3 convolutional layers 422 and upsample the output using a deconvolutional layer 426. This process is repeated for all the other subsequent layers up to the original input resolution where the final output is fed into a 1×1×1 convolutional layer 428 with a softmax activation function to generate voxel-wise semantic predictions 432.

Figure 5A:
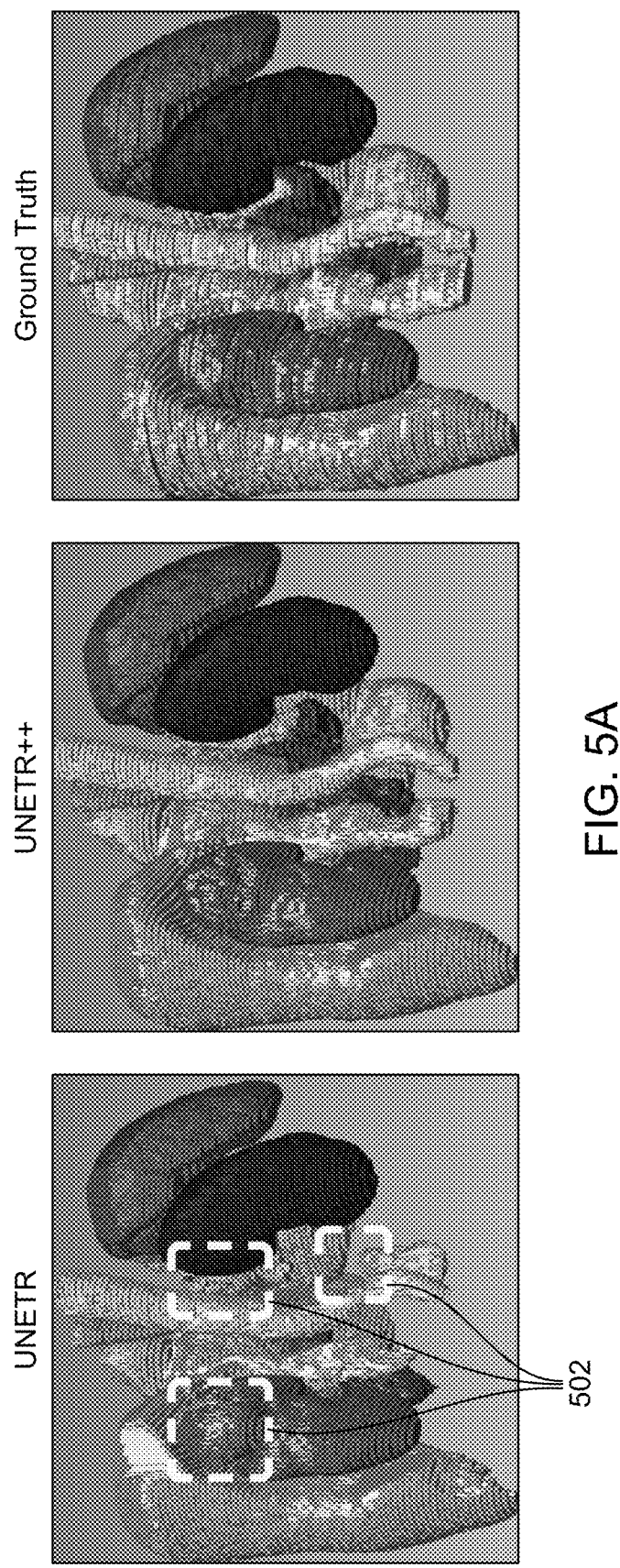
FIGS. 5A and 5B illustrate a qualitative comparison between the UNETR network and the UNETR++ network on Synapse.
Figure 5B:
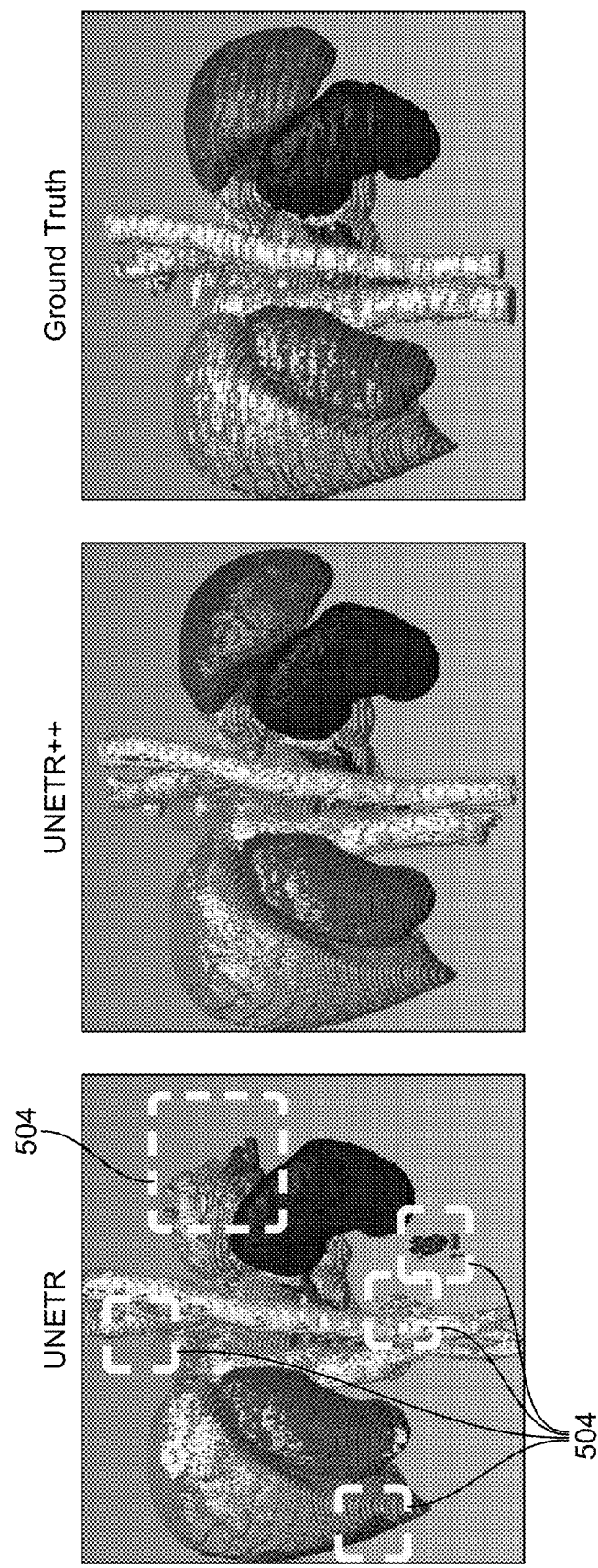

FIGS. 5A, 5B illustrate a qualitative comparison between the UNETR network and the UNETR++ framework on Synapse. See Hatamizadeh et al., *Proceedings of the IEEE/ CVF Winter Conference on Applications of Computer Vision*, 2022, incorporated herein by reference in its entirety.

Two example comparisons between UNETR and UNETR++ are presented containing multiple organs. Each inaccurate segmented region is marked with a dashed box 502, 504. In FIG. 5A, 502, UNETR struggles to accurately segment the right kidney (RKid) and confuses it with gallbladder (Gal). Further, both the stomach (Sto) and left adrenal gland (LAG) tissues are inaccurately segmented. In FIG. 5B, 504, UNETR struggles to segment the whole spleen and mixes it with stomach (Sto) and portal and splenic veins (PSV). Moreover, it under and over-segments certain organs (e.g., PSV and Sto). In comparison, the UNETR++ framework efficiently encodes enriched interdependent spatial and channel features within the EPA block, and accurately segments all organs in these examples. In particular, the UNETR++ framework achieves high-quality segmentation masks with an absolute gain of 8.9% in terms of Dice Similarity Score while significantly reducing the model complexity with a reduction of 54% in terms of parameters and 37% in FLOPs, compared to the UNETR network. See Hatamizadeh et al., Proceedings of the IEEE/CVF Winter Conference on Applications of Computer Vision, 2022.

Figure 6:
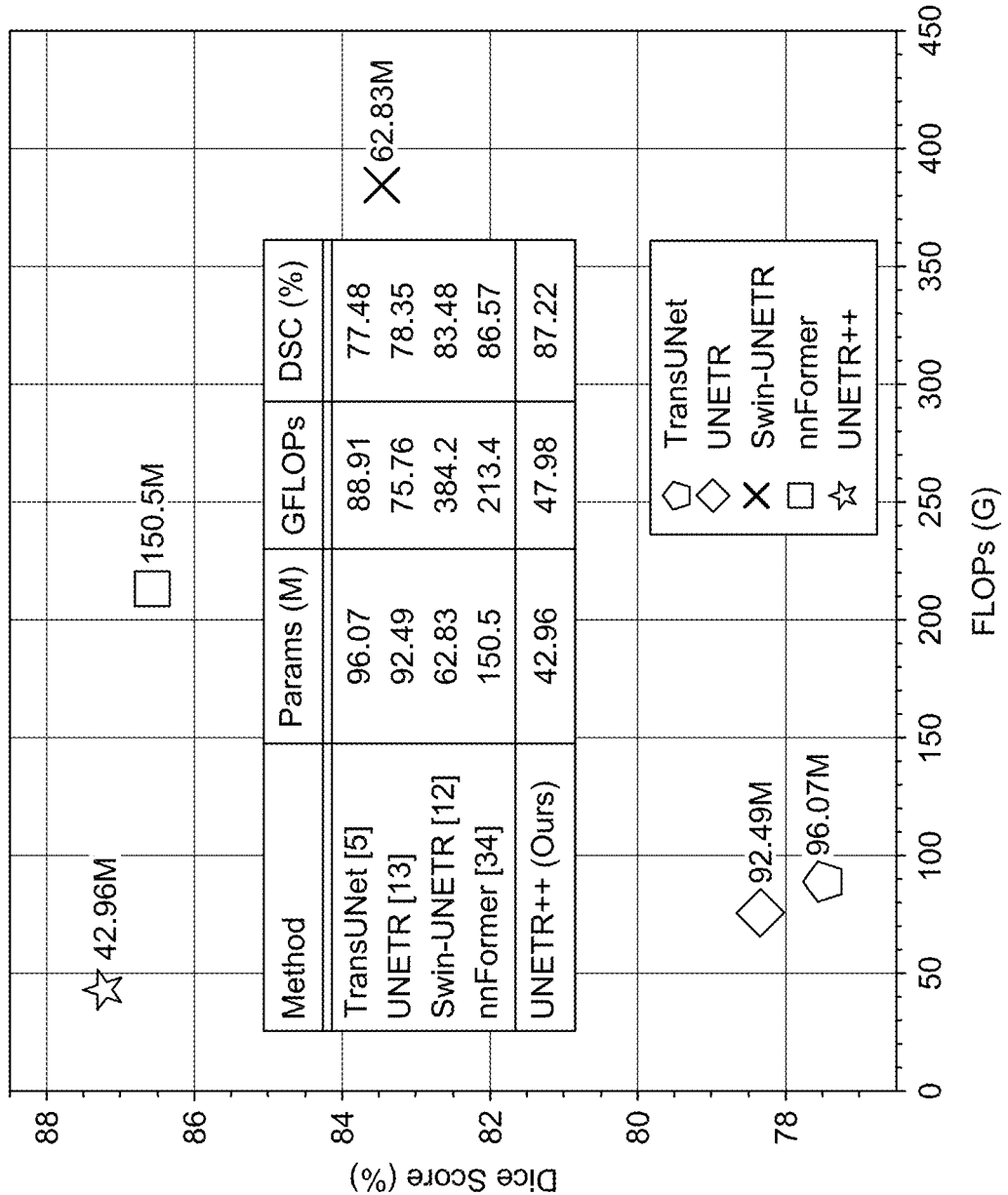
FIG. 6 is a plot of accuracy (Dice score) vs. model complexity (FLOPs and parameters) on the Synapse dataset.

FIG. 6 is a plot of FIG. 5B Accuracy (Dice score) vs. model complexity (FLOPs and parameters) comparison on Synapse. The UNETR++ framework outperforms the best conventional nnFormer method with a considerable reduction in terms of both parameters and FLOPs.

Experimental Setup

Datasets: The Synapse for Multi-organ CT Segmentation dataset is from the MICCAI Multi-Atlas Labeling Beyond the Cranial Vault challenge and consists of abdominal CT scans of 30 subjects with 8 organs. Consistent with previous approaches, the splits follow Chen et al. (2021) and the model is trained on 18 samples and evaluated on the remaining 12 cases. The model performance is reported using Dice Similarity Coefficient (DSC) and 95% Hausdorff Distance (HD95) on 8 abdominal organs: spleen, right kidney, left kidney, gallbladder, liver, stomach, aorta and pancreas. The BTCV for Multi-organ CT Segmentation dataset contains 30 subjects for training/validation and 20 subjects for testing with abdominal CT scans. It consists of 13 organs, including all 8 organs of Synapse dataset, along with esophagus, inferior vena cava, portal and splenic veins, right adrenal gland, and left adrenal gland. The dataset is manually annotated under the supervision of clinical radiologists at Vanderbilt University Medical Center. Each scan comprises 80 to 225 slices, where the spatial size of each slice is 512×512 pixels with a thickness varying from 1 to 6 mm. Each CT scan is independently pre-processed by normalizing the intensities in the range of [−1000, 100]HU to [0, 1] with patch cropping of 128×128×64 and spacing of [0.76, 0.76, 3]. The Dice Similarity Coefficient (DSC) is reported on all 13 abdominal organs. The ACDC for Automated Cardiac Diagnosis dataset comprises cardiac MRI images of 100 patients collected from real clinical exams, along with corresponding segmentation annotations of right ventricle (RV), left ventricle (LV) and myocardium (MYO). See Bernard et al.

The data is split into 70 train images, 10 validation samples and evaluate on 20 remaining samples. The DSC is reported on the three classes. The BraTS comprises of 484 MRI images, where each image consists of four channels, FLAIR, T1w, T1gd and T2w. The dataset is split into 80:5:15 ratio for training, validation and testing and report is provided for the test set. The target categories are whole tumor, enhancing tumor and tumor core. The lung dataset comprises 63 CT volumes for a two-class problem with the goal to segment lung cancer from the background. The data was split into 80:20 ratio for training and validation.

Evaluation Metrics: The performance of the models is measured based on two metrics: Dice Similarity Score (DSC) and 95% Hausdorff Distance (HD95). DSC measures the overlap between the volumetric segmentation predictions and the voxels of the ground truths, it is defined as follows:

$$DSC(Y, P) = 2 * \frac{|Y \cap P|}{|Y| \cap |P|} = 2 * \frac{Y \cdot P}{Y^2 + P^2} \quad (7)$$

where, Y and P denote the ground truths and output probabilities for all voxels, respectively.

HD95 is commonly used as boundary-based metric to measure the 95th percentile of the distances between boundaries of the volumetric segmentation predictions and the voxels of the ground truths. It is defined as follows:

$$HD_{95}(Y, P) = \max\{d_{YP}, d_{PY}\} \quad (8)$$

where, $d_{YP}$ is the maximum $95^{th}$ percentile distance between predicted voxels and the ground truth, and $d_{PY}$ is the maximum $95^{th}$ percentile distance between the ground truth and the predicted voxels.

In one implementation the UNETR++ framework is made using Pytorch v1.10.1 and using the MONAI libraries. See Project-MONAI. Medical open network for ai. github.com/Project-MONAI/MONAI, 2020, incorporated herein by reference in its entirety. For a fair comparison with both the UNETR network and nnFormer, the same input size, pre-processing strategy and no additional training data is used. The models are trained using a single A100 40 GB GPU with input 3D patches of size 128×128×64 for 1k epochs with learning rate of 0.01 and weight decay of $3e^{-5}$. In addition, results are reported with 96×96×96 input size and patch resolution of (4, 4, 4) for BTCV where the models are trained for 5k epochs with learning rate of $1e^{-4}$. Specifically, the input volume is divided into non-overlapping patches during training which are used to learn segmentation maps through back-propagation. During training, the same data augmentations is applied for UNETR, nnFormer and the UNETR++ framework. Further, as in the nnFormer approach, the same deep supervision scheme is used and the loss is computed at multiple resolutions during training. A sliding window is utilized with an overlap ratio of 0:5 during inference.

Baseline Comparison

Table 2 shows the impact of integrating the proposed contributions within the UNETR network on Synapse. The results are shown in terms of segmentation performance (DSC) and model complexity (parameters and FLOPs). For a fair comparison, all results are obtained using the same input size and pre-processing. Integrating the EPA block in the encoders of the hierarchical design improves the segmentation performance to 85.17%. The results are further improved to 87.22% by also introducing the EPA block in decoders. The UNETR++ framework with the novel EPA block both in the encoders and decoders achieves an absolute gain of 8.87% in DSC, while also significantly reducing the model complexity. In addition to the Dice Similarity Coefficient (DSC), the model complexity is reported in terms of parameters and FLOPs. In all cases, performance is reported in terms of single model accuracy. As discussed earlier, UNETR++ is a hierarchical architecture that downsamples the feature maps of the encoder by a factor of two after each stage. Hence, the model comprises four encoder stages and four decoder stages. This hierarchical design of the UNETR++ framework enables a significant reduction in model complexity by reducing the parameters from 92.49M to 16.60M and FLOPs from 75.76G to 30.75G while maintaining a comparable DSC of 78.29%, compared to the baseline. Introducing the EPA block within the UNETR++ framework encoders leads to a significant improvement in performance with an absolute gain of 6.82% in DSC over the baseline. The performance is further improved by integrating the EPA block in the decoder. The final UNETR++ framework has a hierarchical design with the novel EPA block both in encoders and decoders leads to a significant improvement of 8.87% in DSC, while considerably reducing the model complexity by 54% in parameters and 37% in FLOPs, compared to the UNETR network. An experiment is conducted to evaluate the spatial and channel attention within the EPA block. Employing spatial and channel attention improve the performance significantly with DSC of 86.42% and 86.39%, respectively over the baseline. Combining both spatial and channel attention within the EPA block leads to a further improvement with DSC of 87.22%.

al., In Proceedings of the *IEEE/CVF Winter Conference on Applications of Computer Vision* (2022); and Ali Hatamizadeh et al., In *International MICCAI Brainlesion Workshop* (2022). On this dataset, nnFormer obtains superior performance compared to other existing works. The UNETR++ framework outperforms nnFormer by achieving a DSC of 87.22%. Further, UNETR++ obtains an absolute reduction in error of 3.1% over nnFormer in terms of HD95 metric. Notably, UNETR++ achieves this improvement in segmentation performance by significantly reducing the model complexity by over 71% in terms of parameters and FLOPs.

TABLE 1

State-of-the-art comparison on the abdominal multi-organ Synapse dataset.

| Methods | Params | FLOPs | Spl | RKid | LKid | Gal | HD95↓ | DSC↑ |
|---|---|---|---|---|---|---|---|---|
| U-Net | — | — | 86.87 | 68.60 | 77.77 | 69.72 | — | 76.85 |
| TransUNet | 96.07 | 88.91 | 85.08 | 77.02 | 81.87 | 63.16 | 31.69 | 77.49 |
| Swin-UNet | — | — | 90.66 | 79.61 | 83.28 | 66.53 | 21.55 | 79.13 |
| UNETR | 92.49 | 75.76 | 85.00 | 84.52 | 85.60 | 56.30 | 18.59 | 78.35 |
| MISSFormer | — | — | 91.92 | 82.00 | 85.21 | 68.65 | 18.20 | 81.96 |
| Swin-UNETR | 62.83 | 384.2 | 95.37 | 86.26 | 86.99 | 66.54 | 10.55 | 83.48 |
| nnFormer | 150.5 | 213.4 | 90.51 | 86.25 | 86.57 | 70.17 | 10.63 | 86.57 |
| UNETR++ | 42.96 | 47.98 | 95.77 | 87.18 | 87.54 | 71.25 | 7.53 | 87.22 |

| Methods | Params | FLOPs | Liv | Sto | Aor | Pan | HD95↓ | DSC↑ |
|---|---|---|---|---|---|---|---|---|
| U-Net | — | — | 93.43 | 75.58 | 89.07 | 53.98 | — | 76.85 |
| TransUNet | 96.07 | 88.91 | 94.08 | 75.62 | 87.23 | 55.86 | 31.69 | 77.49 |
| Swin-UNet | — | — | 94.29 | 76.60 | 85.47 | 56.58 | 21.55 | 79.13 |
| UNETR | 92.49 | 75.76 | 94.57 | 70.46 | 89.80 | 60.47 | 18.59 | 78.35 |
| MISSFormer | — | — | 94.41 | 80.81 | 86.99 | 65.67 | 18.20 | 81.96 |
| Swin-UNETR | 62.83 | 384.2 | 95.72 | 77.01 | 91.12 | 68.80 | 10.55 | 83.48 |
| nnFormer | 150.5 | 213.4 | 96.84 | 86.83 | 92.04 | 83.35 | 10.63 | 86.57 |
| UNETR++ | 42.96 | 47.98 | 96.42 | 86.01 | 92.52 | 81.10 | 7.53 | 87.22 |

Abbreviations stand for: Spl: spleen, RKid: right kidney, LKid: left kidney, Gal: gallbladder, Liv: liver, Sto: stomach, Aor: aorta, Pan: pancreas.
Best results are in bold.

Figures 7A, 7B:
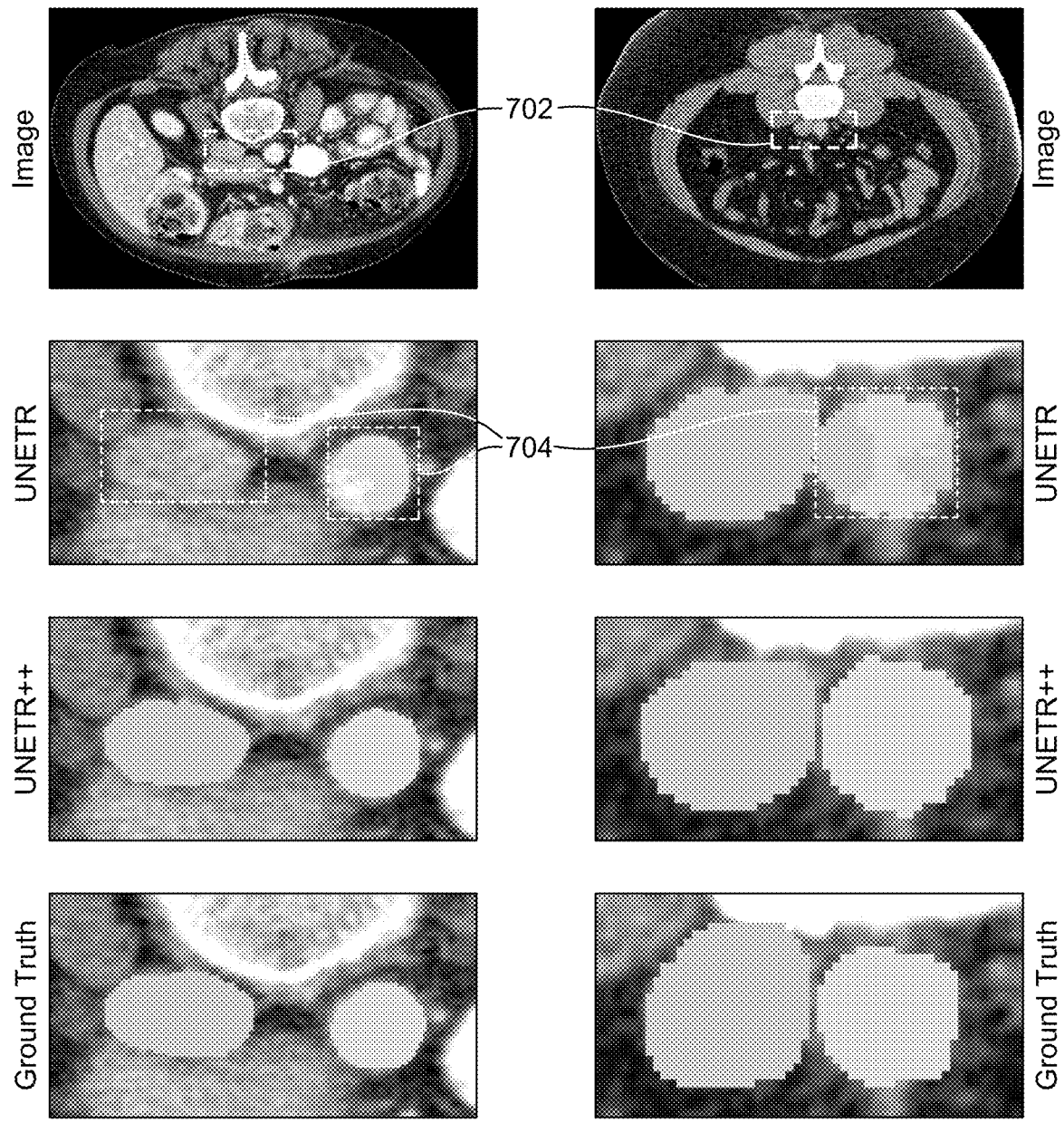
FIGS. 7A-7D illustrate a qualitative comparison between the UNETR network and the UNETR++ network on the Synapse dataset.
Figures 7C, 7D:
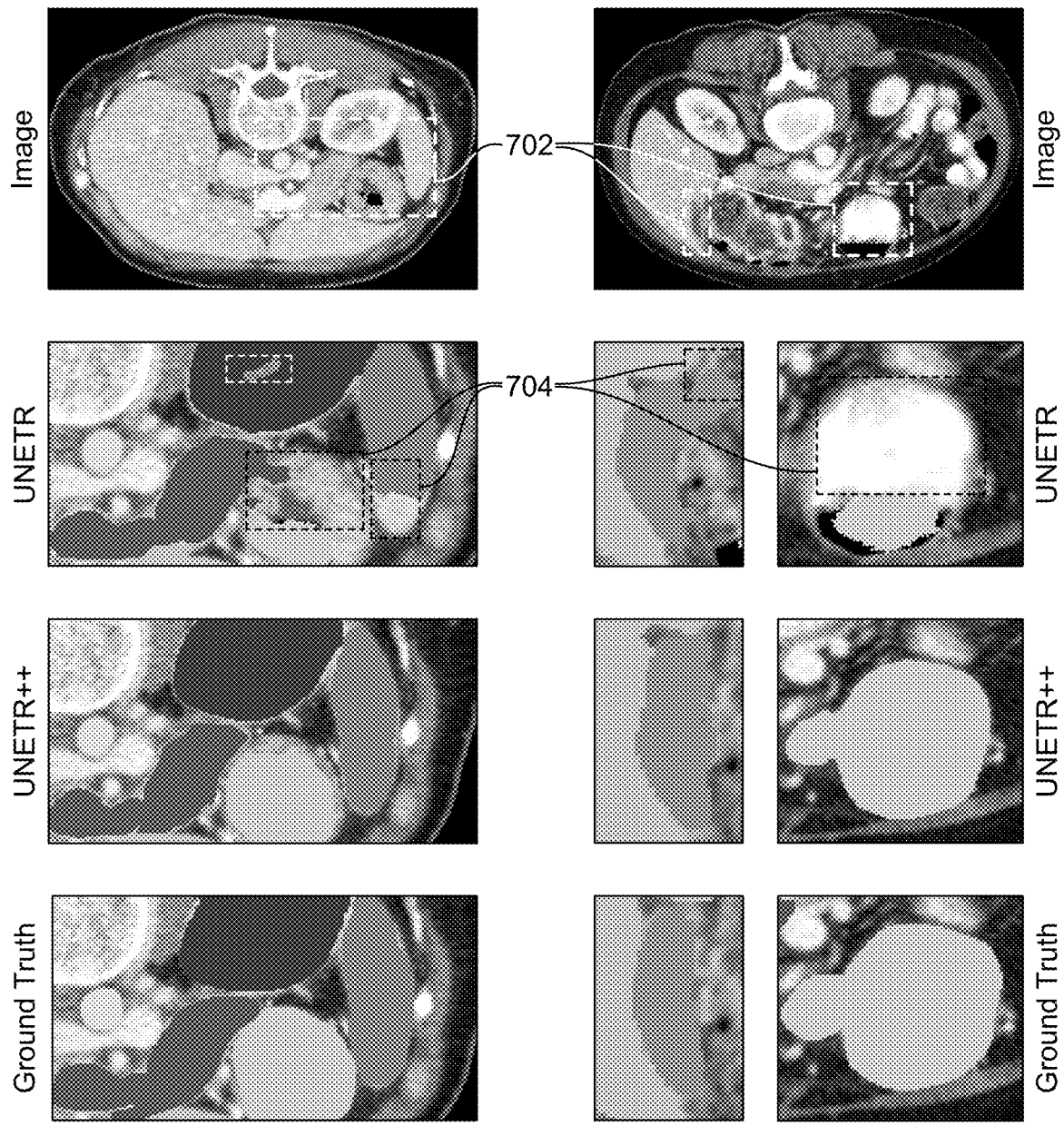

FIGS. 7A-7D shows a qualitative comparison between the baseline and the UNETR++ framework on the Synapse dataset. Different organs (marked with dashed boxes 702 in the first row) are enlarged from several cases. The inaccurate segmentations are marked by dashed boxes 704. In FIG. 7A, the UNETR network struggles to segment the inferior vena cava and aorta. In FIG. 7B, it confuses the same two organs when they are adjacent to each other. In FIGS. 7C, 7D, the baseline under-segments left kidney, spleen and stomach, whereas it over-segments the gallbladder. In contrast, the UNETR++ framework achieves improved performance by accurately segmenting all organs.

State-of-the-Art Comparison

Table 1 shows the results on the multiorgan Synapse dataset. The UNETR++ framework achieves favorable segmentation performance against existing methods, while considerably reducing the model complexity. The segmentation performance is reported using DSC and HD95 metrics on the abdominal organs. In addition, the model complexity is reported in terms of parameters and FLOPs for each method. The segmentation performance is reported with a single model accuracy and without utilizing any pre-training, model ensemble or additional data. The pure CNN-based U-Net approach achieves a DSC of 76.85%. See Ronneberger et al. Among existing hybrid transformers-CNN based methods, UNETR and Swin-UNETR achieve DSC of 78.35% and 83.48%, respectively. See Ali Hatamizadeh, et al., In Proceedings of the *IEEE/CVF Winter Conference on Applications of Computer Vision* (2022); Xiaohong Huang, Zhifang Deng, Dandan Li, and Xueguang Yuan. Missformer: An effective medical image segmentation transformer. *arXiv preprint arXiv*:2109.07162, 2021; Ali Hatamizadeh et al., In *International MICCAI Brainlesion Workshop* (2022); and Zhao et al. (2021), each incorporated herein by reference in their entirety.

TABLE 2

Baseline comparison on Synapse.

| Model | Params (M) | FLOPS (G) | DSC (%) |
|---|---|---|---|
| UNETR (Baseline) | 92.49 | 75.76 | 78.35 |
| +EPA in Encoder | 28.94 | 39.36 | 85.17 |
| +EPA in Decoder (UNETR++) | 42.96 | 47.98 | 87.22 |

TABLE 3

State-of-the-art comparison on the BTCV test set for multi-organ segmentation.

| Methods | Spl | RKid | LKid | Gal | Eso | Liv | Sto | Aor |
|---|---|---|---|---|---|---|---|---|
| nnU-Net | 95.95 | 88.35 | 93.02 | 70.13 | 76.72 | 96.51 | 86.79 | 88.93 |
| TransBTS | 94.55 | 89.20 | 90.97 | 68.38 | 75.61 | 96.44 | 83.52 | 88.55 |

TABLE 3-continued

State-of-the-art comparison on the BTCV
test set for multi-organ segmentation.

| | | | | | | | | |
|---|---|---|---|---|---|---|---|---|
| UNETR | 90.48 | 82.51 | 86.05 | 58.23 | 71.21 | 94.64 | 72.06 | 86.57 |
| Swin-UNETR | 94.59 | 88.97 | 92.39 | 65.37 | 75.43 | 95.61 | 75.57 | 88.28 |
| nnFormer | 94.58 | 88.62 | 93.68 | 65.29 | 76.22 | 96.17 | 83.59 | 89.09 |
| UNETR++ | 94.94 | 91.90 | 93.62 | 70.75 | 77.18 | 95.95 | 85.15 | 89.28 |

| Methods | IVC | PSV | Pan | RAG | LAG | Avg |
|---|---|---|---|---|---|---|
| nnU-Net | 82.89 | 78.51 | 79.60 | 73.26 | 68.35 | 83.16 |
| TransBTS | 82.48 | 74.21 | 76.02 | 67.23 | 67.03 | 81.31 |
| UNETR | 76.51 | 70.37 | 66.06 | 66.25 | 63.04 | 76.00 |
| Swin-UNETR | 81.61 | 76.30 | 74.52 | 68.23 | 66.02 | 80.44 |
| nnFormer | 80.80 | 75.97 | 77.87 | 70.20 | 66.05 | 81.62 |
| UNETR++ | 83.14 | 76.91 | 77.42 | 72.56 | 68.17 | 83.28 |

Abbreviations are as follows: Spl: spleen, RKid: right kidney, LKid: left kidney, Gal: gallbladder, Eso: esophagus, Liv: liver, Sto: stomach, Aor: aorta, IVC: the inferior vena cava, PSV: portal and splenic veins, Pan: pancreas, RAG: right adrenal gland, LAG: left adrenal gland.
Results are obtained from BTCV leaderboard. Best results are in bold.

See Isensee et al.; WenxuanWang, Chen Chen, Meng Ding, Hong Yu, Sen Zha, and Jiangyun Li. Transbts: Multimodal brain tumor segmentation using transformer. In *International Conference on Medical Image Computing and Computer-Assisted Intervention*, 2021; Ali Hatamizadeh, et al., In Proceedings of the *IEEE/CVF Winter Conference on Applications of Computer Vision* (2022); Ali Hatamizadeh et al., In *International MICCAI Brainlesion Workshop* (2022); and Zhou et al. (2021), each incorporated herein by reference in their entirety.

Figure 8C:
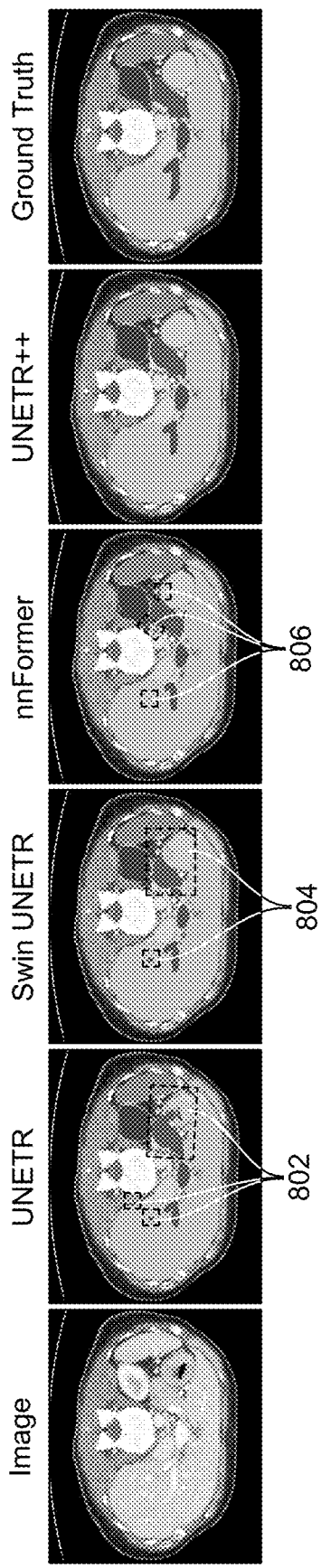

FIGS. 8A, 8B, 8C shows a qualitative comparison on multi-organ segmentation task. Here, the UNETR++ framework is compared with conventional methods: UNETR, Swin UNETR, and nnFormer. The different abdominal organs are shown in the legend below the examples. Existing methods struggle to correctly segment different organs (marked in dashed box 802, 804, 806). In FIG. 8A, it can be seen that conventional approaches struggle to accurately segment the stomach by either under-segment it in the case of UNETR and Swin UNETR or confusing it with spleen in the case of nnFormer. In comparison, the UNETR++ framework accurately segments the stomach. Further, conventional methods fail to fully segment the right kidney in FIG. 8B. In contrast, the UNETR++ framework accurately segments the whole right kidney, likely due to learning the contextual information with the enriched spatial-channel representation. Moreover, the UNETR++ framework smoothly delineates boundaries between spleen, stomach and liver. In FIG. 8C, UNETR confuses stomach with pancreas. On the other hand, Swin UNETR and nnFormer under-segment stomach and left adrenal gland, respectively. The UNETR++ framework accurately segments all organs with better delineation of the boundaries in these examples.

BTCV Dataset: Table 3 presents the comparison on BTCV test set. The UNETR++ achieves favorable segmentation performance against existing 3D image segmentation methods. Here, all results are based on a single model accuracy without any ensemble, pre-training or additional data. The results on all 13 organs are reported along with corresponding mean performance over all organs. Among existing works, UNETR and SwinUNETR achieve a mean DSC of 76.0% and 80.44%. Among existing methods, nnUNet obtains a performance of 83.16% mean DSC, but requires 358G FLOPS. In comparison, the UNETR++ framework performs favorably against nnUNet by achieving a mean DSC of 83.28%, while requiring significantly fewer FLOPs of 31G.

ACDC Dataset: Table 4 shows the comparison on ACDC. The performance on right ventricle (RV), left ventricle (LV) and myocardium (MYO) are reported along with mean results using DSC metric. The UNETR++ framework obtains better results compared to existing methods by achieving a mean DSC of 90.73%. Here, all results are reported with a single model accuracy and without using any pre-training, model ensemble or additional data. UNETR and nnFormer achieve mean DSC of 86.61% and 92.06%, respectively. The UNETR++ framework achieves improved performance with a mean DSC of 92.83%.

TABLE 4

State-of-the-art comparison on ACDC. Best results are in bold.

| Methods | RV | Myo | LV | Average |
|---|---|---|---|---|
| TransUNet | 88.86 | 84.54 | 95.73 | 89.71 |
| Swin-UNet | 88.55 | 85.62 | 95.83 | 90.00 |
| UNETR | 85.29 | 86.52 | 94.02 | 86.61 |
| MISSFormer | 86.36 | 85.75 | 91.59 | 87.90 |
| nnFormer | 90.94 | 89.58 | 95.65 | 92.06 |
| UNETR++ | 91.89 | 90.61 | 96.00 | 92.83 |

See Chen et al. (2021); Cao et al.; Ali Hatamizadeh, et al., In Proceedings of the *IEEE/CVF Winter Conference on Applications of Computer Vision* (2022); Huang et al. (2021); and Zhou et al. (2021).

BRaTs Dataset: Table 5 shows segmentation performance, model complexity, and inference time. For a fair comparison, the same input size and pre-processing strategy are used.

Speed comparison is made on Quadro RTX 6000 24 GB GPU and 32 Core Intel® Xeon® 4215 CPU. Here inference time is average forward pass time using 1×128×128×128 input size of BRaTs. Compared to recent transformer-based methods, the UNETR++ achieves favorable performance while operating at a faster inference speed as well as requiring significantly lesser GPU memory. In particular, UNETR++ achieves favorable segmentation results (DSC), while being efficient (Params in millions and GFLOPS), operating at faster inference speed (GPU T. and CPU T. in ms) and requires lesser GPU memory (Mem in GB).

TABLE 5

Comparison on BRaTs.

| Model | Params | FLOPs | Mem | GPU T | CPU T | DSC (%) |
|---|---|---|---|---|---|---|
| UNETR | 92.5 | 153.5 | 3.3 | 82.5 | 2145.0 | 81.2 |
| Swin-UNETR | 62.8 | 572.4 | 10.7 | 228.6 | 7612.3 | 81.5 |
| nnFormer | 149.6 | 421.5 | 12.6 | 148.0 | 5247.5 | 82.3 |
| UNETR++ | 42.6 | 70.1 | 2.4 | 62.4 | 1497.7 | 82.8 |

Lungs Dataset: UNETR++ and other SOTA models are evaluated on the lung cancer segmentation task. UNETR++ obtains better segmentation performance compared to existing methods by achieving a mean DSC of 80.68%.

TABLE 6

Comparison on Lungs Dataset

| Model | DSC (%) |
|---|---|
| nnUNet | 74.31 |
| SwinUNETR | 75.55 |
| nnFormer | 77.95 |

TABLE 6-continued

Comparison on Lungs Dataset

| Model | DSC (%) |
|---|---|
| UNETR | 73.29 |
| UNETR++ | 80.68 |

Qualitative Results

Additional qualitative comparisons are provided for Synapse and ACDC datasets between UNETR++ and the state-of-the-art methods. Moreover, a detailed comparison is provided between UNETR++ and the baseline using visualizations enlarged on specific organs for both datasets.

Figure 9A:
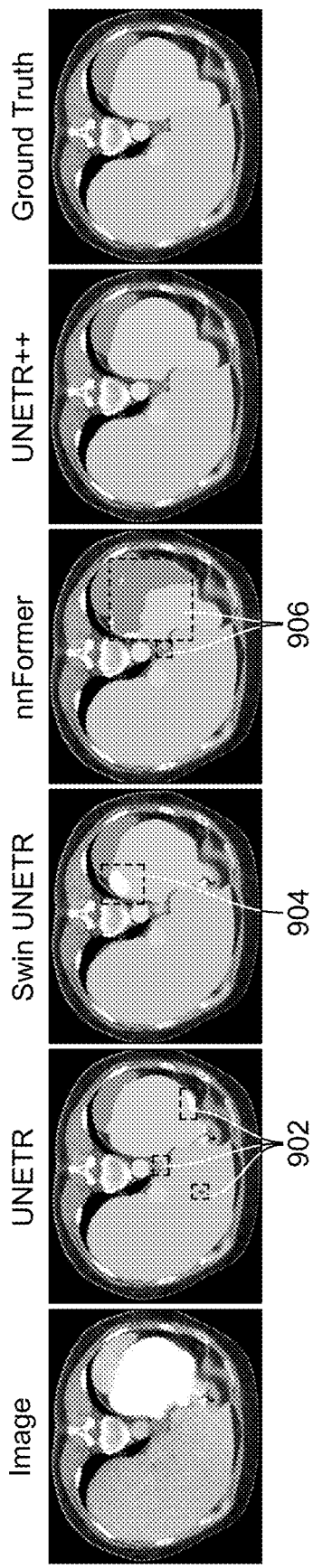
FIGS. 9A-9E illustrate qualitative comparisons for different cases between the UNETR++ network and conventional approaches on the Synapse dataset.
Figure 9B:
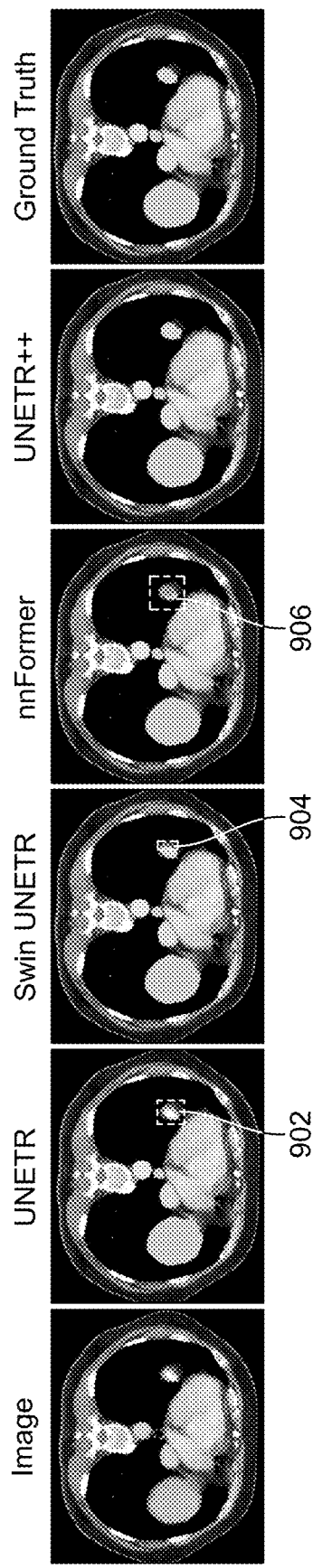
Figure 9C:
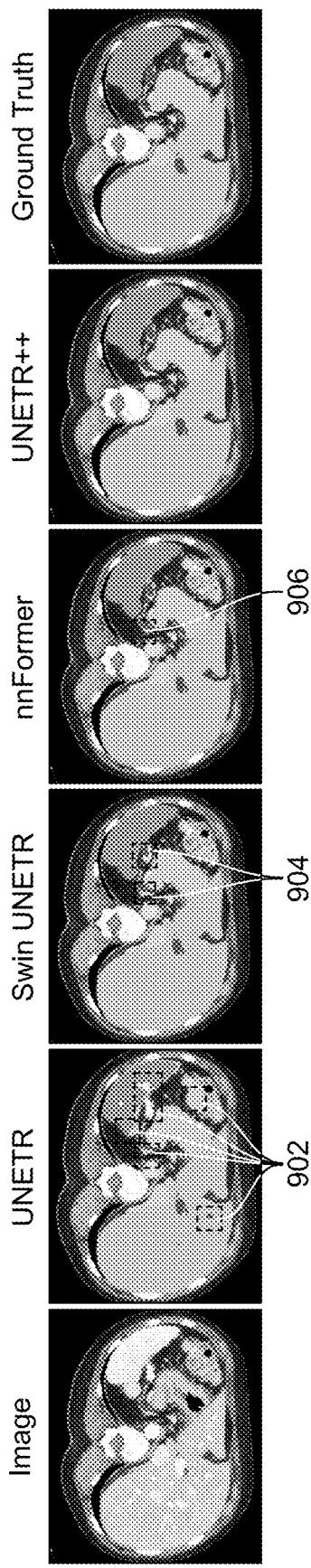
Figure 9D:
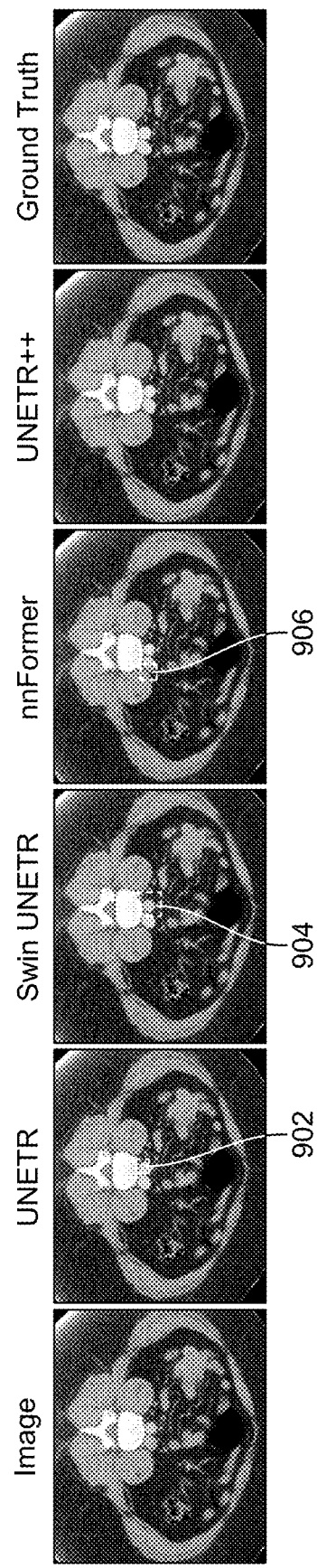
Figure 9E:
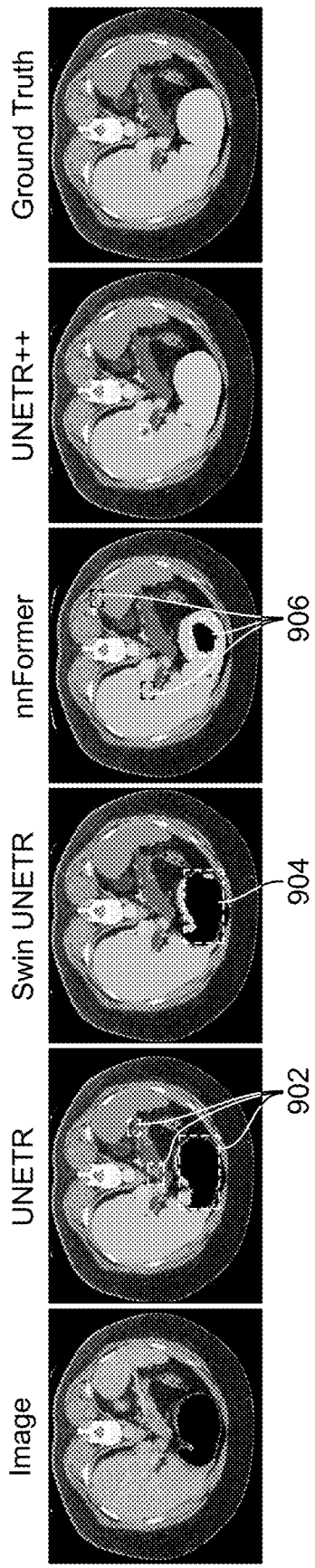

FIGS. 9A-9E illustrate qualitative comparisons for different cases between the UNETR++ framework and existing approaches on Synapse dataset. The inaccurate predictions are marked with dashed boxes 902, 904, 906. In FIGS. 9A, 9B, the UNETR++ framework differentiates the stomach tissues at different sizes and spleen successfully, while nnFormer struggles to differentiate between spleen and stomach, UNETR and Swin UNETR struggle to differentiate between stomach and the background, demonstrating that UNETR++ provides better segmentation predictions at different scales. In FIG. 9C, the UNETR++ framework accurately segments all the organs, while the other conventional methods under-segments left adrenal gland or spleen, and over-segments stomach in the case of UNETR. As illustrated in FIG. 9D, the UNETR++ framework well delineates the boundaries of the inferior vena cava, compared to all conventional methods which struggle, and confuse it with the background. In FIG. 9E, the conventional methods under-segment the stomach in addition to confusing pancreas and portal and splenic veins in the case of UNETR. As illustrated, the UNETR++ framework has a better delineation of the boundaries of different organs without under/over-segmenting, thus suggesting that the UNETR++ framework encodes enriched inter-dependent spatial and channel features within the EPA block.

Figure 10A:
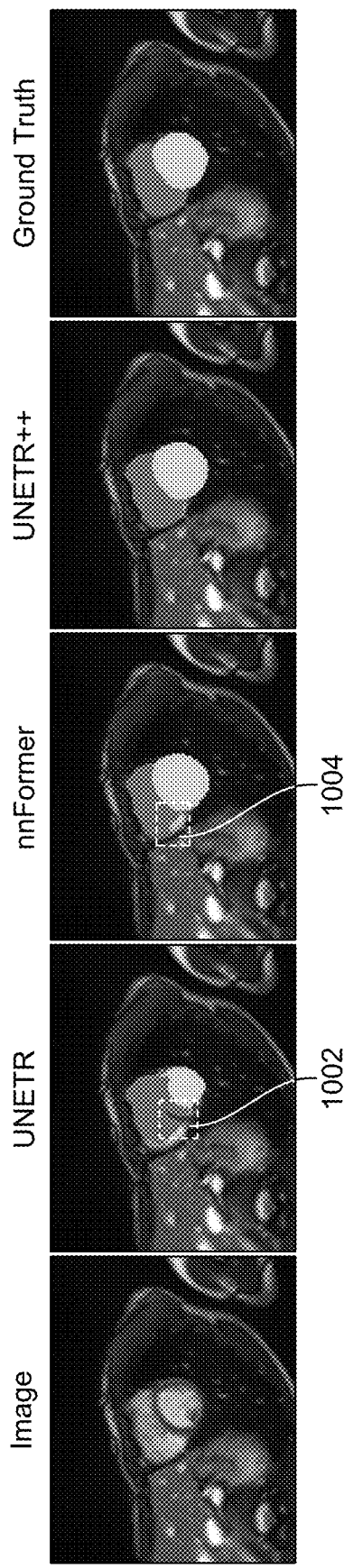
FIGS. 10A-10C illustrates qualitative comparisons for different cases between the UNETR++ network and conventional approaches, nnFormer and the UNETR network on the ACDC dataset.
Figure 10B:
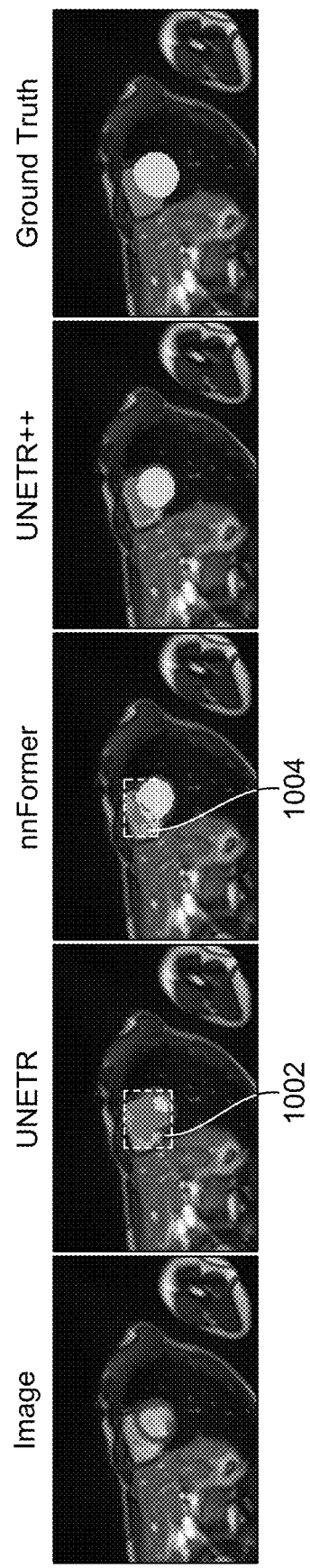
Figure 10C:
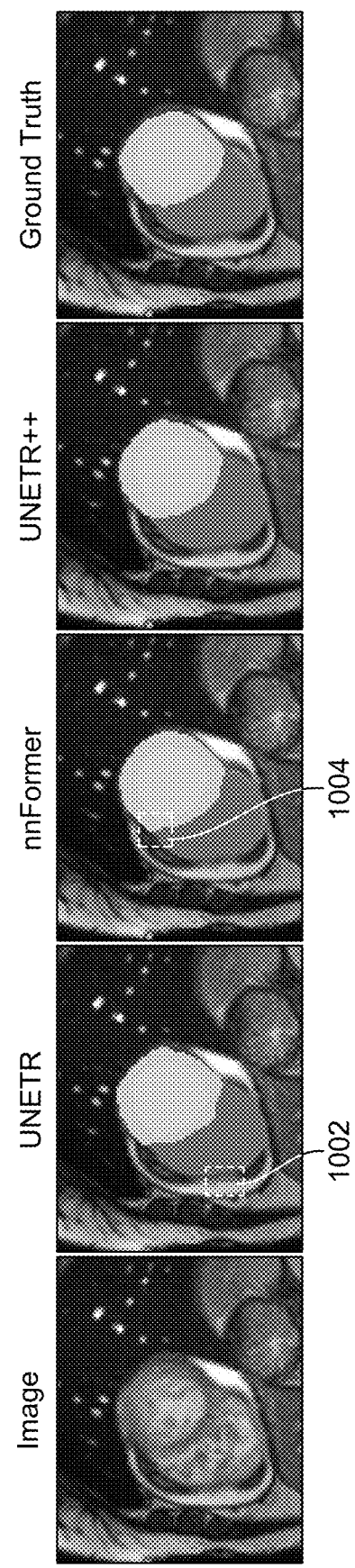

FIGS. 10A-10C illustrate qualitative comparisons for different cases between UNETR++ and existing approaches, nnFormer and UNETR on the ACDC dataset. The inaccurate predictions are marked with dashed boxes 1002, 1004. In FIG. 10A, UNETR and nnFormer under-segments the right ventricular (RV) cavity, while the UNETR++ framework accurately segments all three categories. In FIG. 10B, a difficult sample is presented where the sizes of all three heart segments are comparatively smaller. In this case, both UNETR and nnFormer under-segments and struggles to delineate between the segments, while UNETR++ gives a better segmentation. In FIG. 10C, a simpler sample is presented. However, the conventional methods over-segment the RV cavity and the myocardium in this case, while the UNETR++ framework provides better delineation and provides a segmentation very close to the ground truth. Similar to the observation from Synapse, these qualitative examples show that, UNETR++ achieves delineation for the three heart segments without under-segmenting or over-segmenting, thus suggesting the importance of its inter-dependent spatial and channel features encoded in the EPA block.

Figures 11A, 11B:
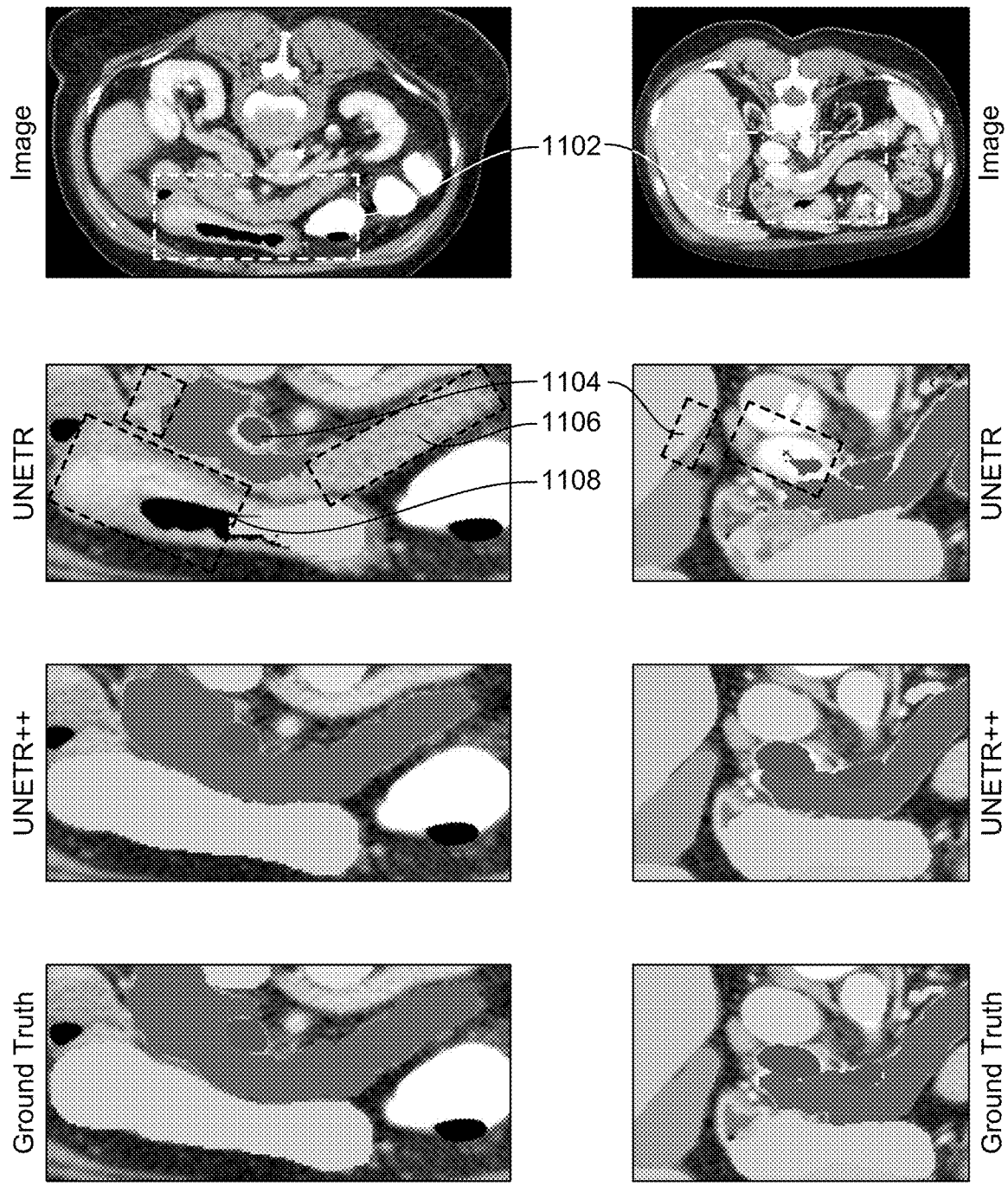
FIGS. 11A-11E illustrate a qualitative comparison between the UNETR++ network and the UNETR network on Synapse dataset.
Figures 11C, 11D:
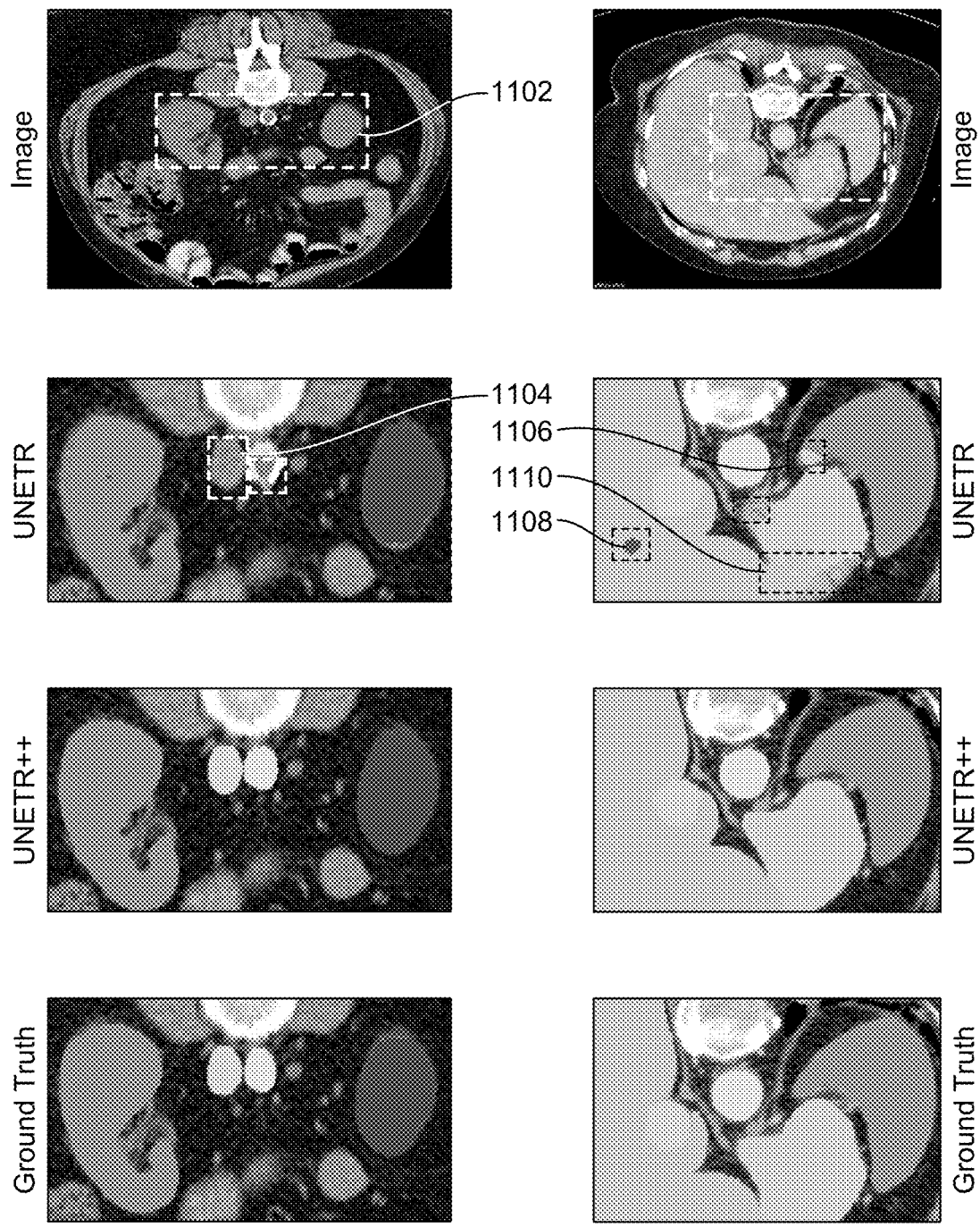
Figure 11E:
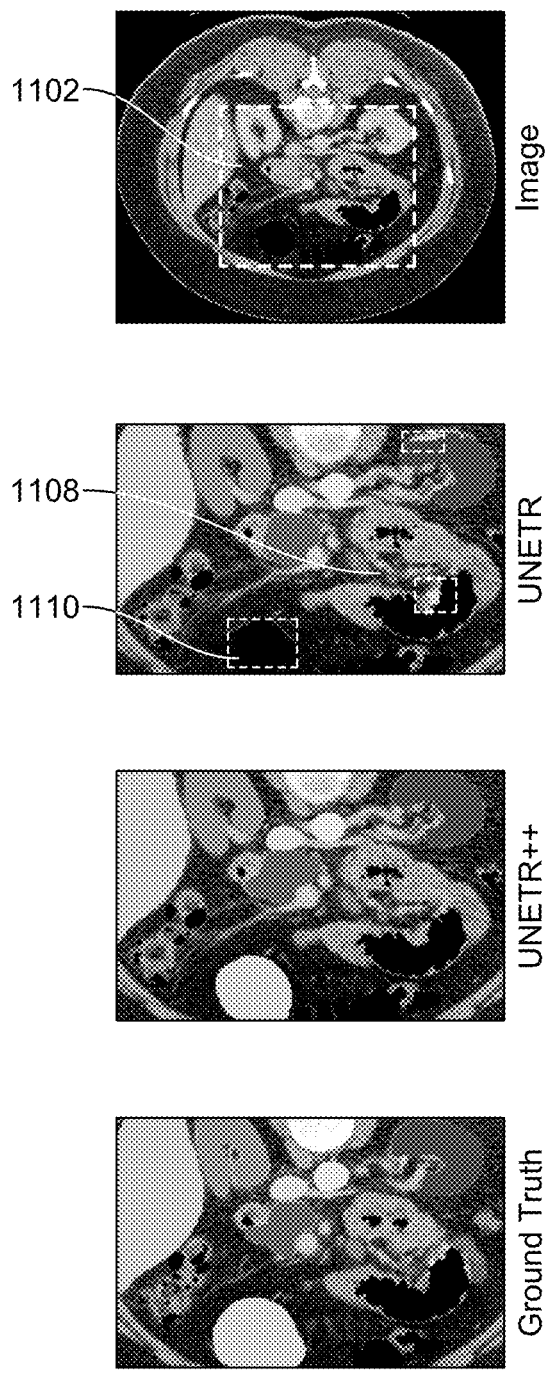

Detailed qualitative comparison between UNETR++ and UNETR FIGS. 11A-11E illustrate a qualitative comparison between the UNETR++ framework and the UNETR network on Synapse dataset. Visualizations are presented on an enlarged view of different organs (marked with dashed boxes 1102, 1104, 1106, 1108, 1110 from several cases for better analysis. In FIG. 11A, UNETR++ delineates the outline of pancreas well, while the UNETR network notably struggles in segmenting the pancreas and under-segments the stomach. In FIG. 11B, the and splenic veins, while UNETR++ segments these organs precisely. In FIG. 11C, the baseline struggles to segment the inferior vena cava and aorta. In FIGS. 11D, 11E, the UNETR network under-segments stomach and struggles in delineating the boundaries of spleen and left kidney. On the other hand, UNETR++ achieves improved performance and accurately segments all these organs with better delineation.

Figure 12A:
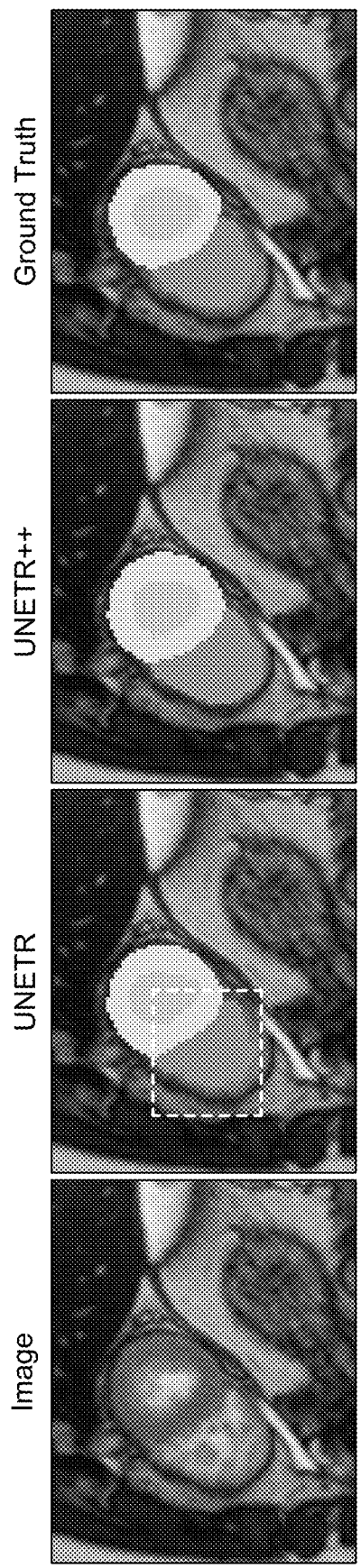
FIGS. 12A-12C is a qualitative comparison between the UNETR++ network and the UNETR network on the ACDC dataset.
Figure 12B:
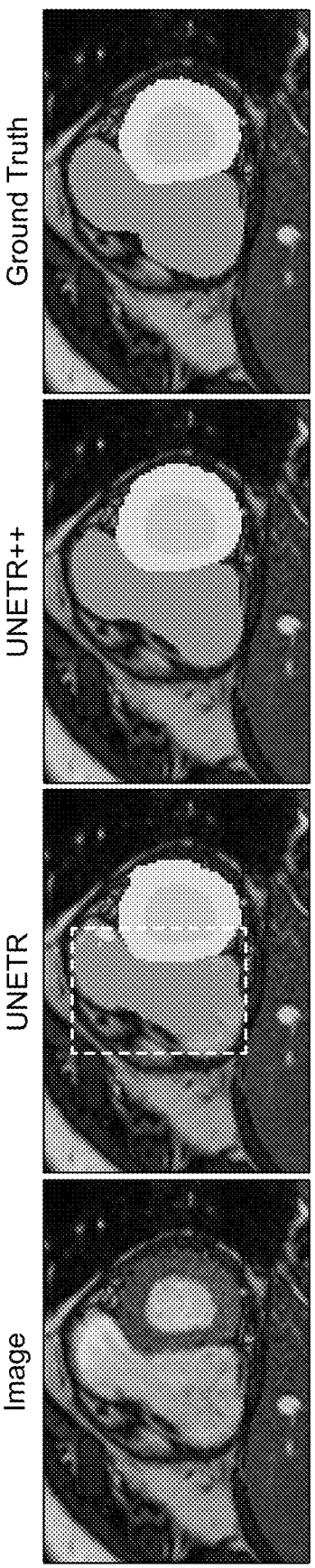
Figure 12C:
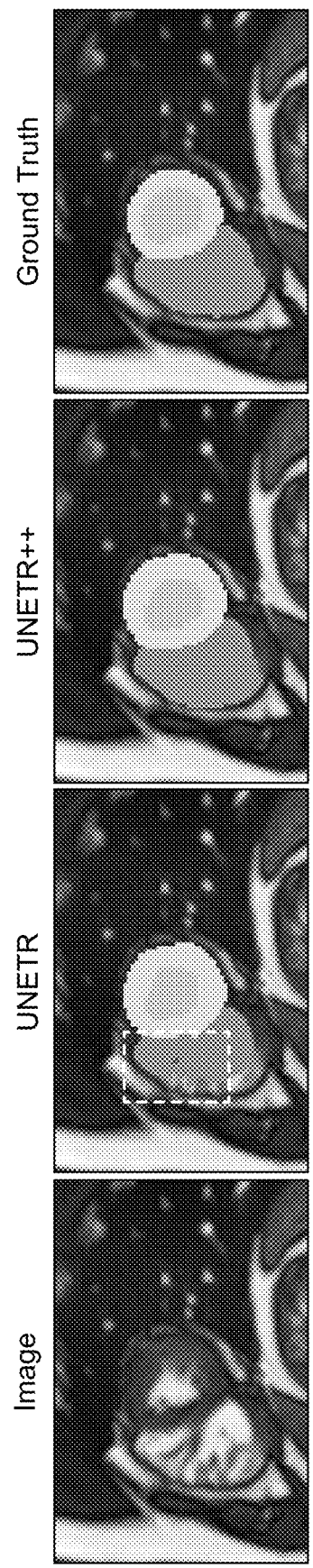

FIGS. 12A-12C show qualitative comparison between the UNETR++ framework and the UNETR network on the ACDC dataset. In all three Figures, UNETR suffers from under-segmentation and struggles in delineating the boundaries of the right ventricular (RV) cavity, while UNETR++ segments all three segments more precisely.

Figure 13A:
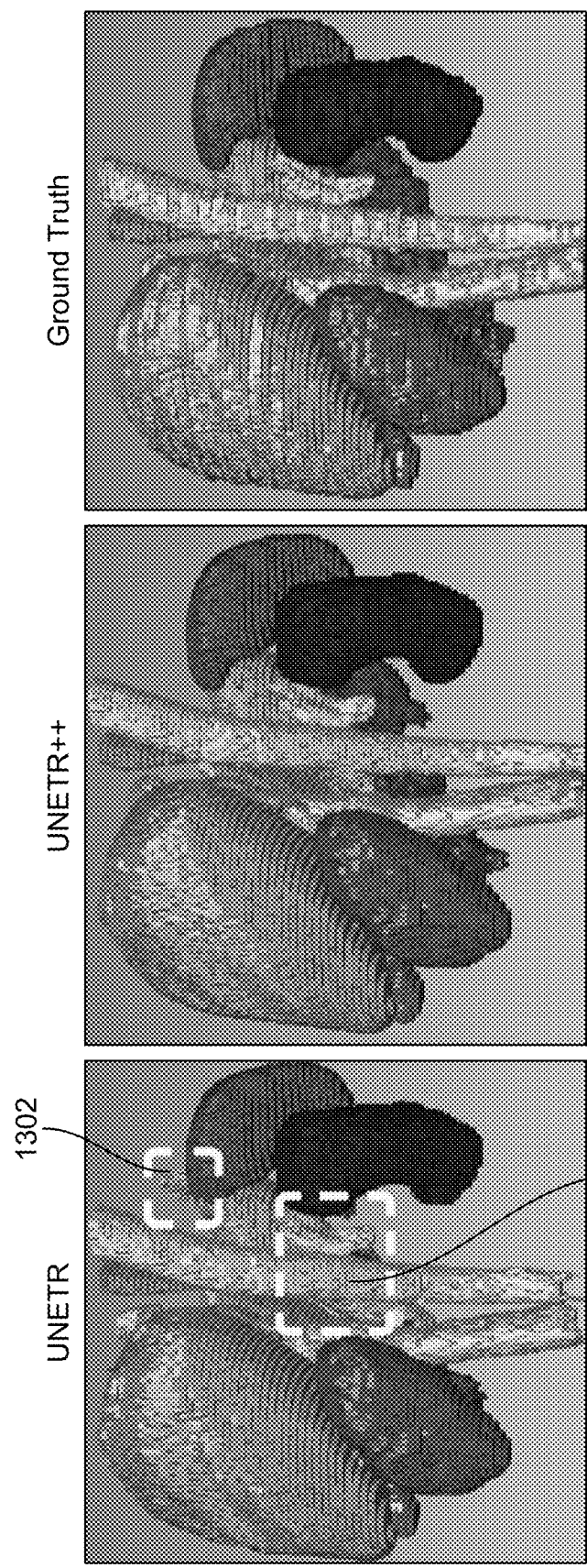
FIGS. 13A and 13B illustrate the 3D rendered segmentation results of the UNETR++ network in comparison to the UNETR network.
Figure 13B:
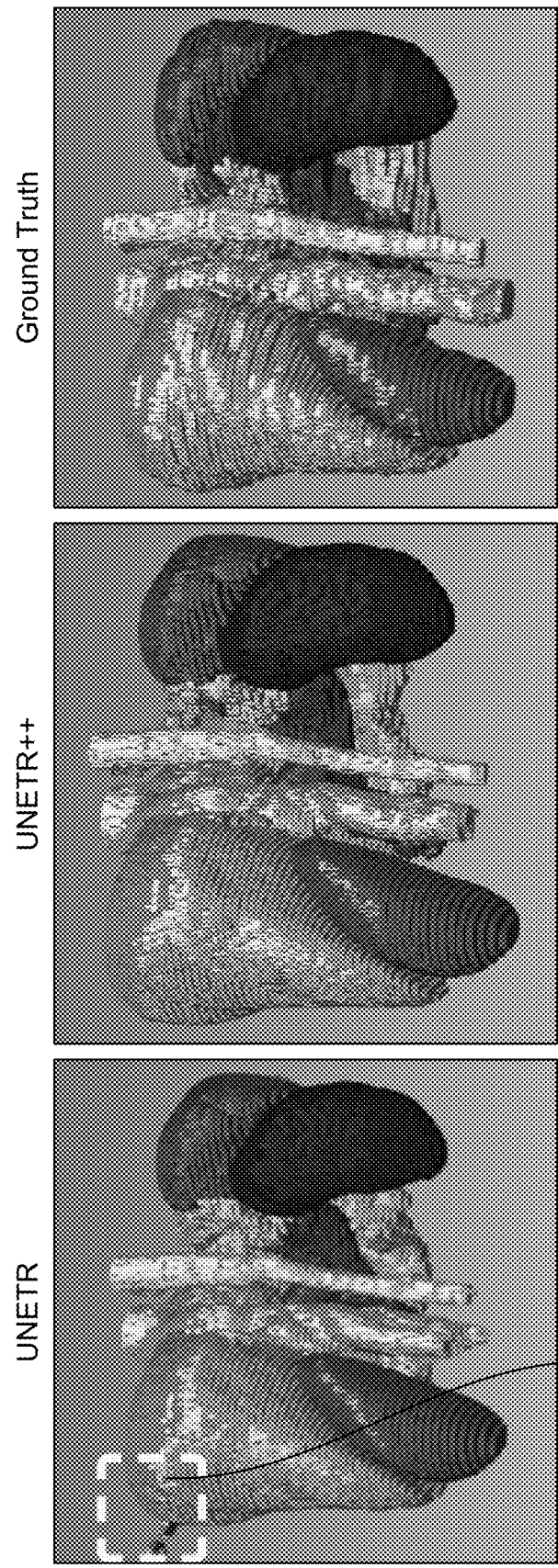

The 3D rendered segmentation results of UNETR++ are further illustrated in comparison to the UNETR network. FIGS. 13A, 13B illustrate qualitative comparison between the baseline UNETR and the UNETR++ framework on Synapse dataset. Each inaccurate segmented region is marked with a dashed box 1302, 1304.

Ablations

To investigate the scalability of the UNETR++ framework, an experiment was conducted with feature maps of size [64, 128, 256, 512] instead of [32, 64, 128, 256] on the BTCV dataset. Although the number of parameters with this change increased to 94:24M and the FLOPs increased to 117G, the average dice similarity score (DSC) is improved from 83.28% to 84.27%, which proves the scalability of UNETR++ without using any ensemble, pre-training or additional custom data.

As such, UNETR++ introduces an efficient paired attention (EPA) block to encode enriched inter-dependent spatial and channel features by using spatial and channel attention. Within the EPA block, the weights of query and key mapping functions are shared to better communicate between spatial and channel branches, providing complementary benefits as well as reducing the parameters.

To validate the effectiveness of the EPA block, experiments were conducted on Synapse to compare the EPA module with other attention methods. (i) integrate the gated attention (GA) from the attention-gated U-Net method within nnUNET (referred to col. 3 in Table 7). (ii) replace the EPA module in UNETR++, over the proposed hierarchical approach, with GA (column 4 in Table 6 and with squeeze-and-excitation (SE) (col. 5 in Table Z). The UNETR++ achieves favorable segmentation results on five datasets while significantly reducing the model complexity, compared to conventional methods.

TABLE 7

Comparison with other attention methods on Synapse

| Model | nnUNet | Attention nnUNet | EPA replaced w/ GA | EPA replaced w/ SE | UNETR++ |
|---|---|---|---|---|---|
| DSC | 84.2 | 85.0 | 85.3 | 85.5 | 87.2 |

Figure 14A:
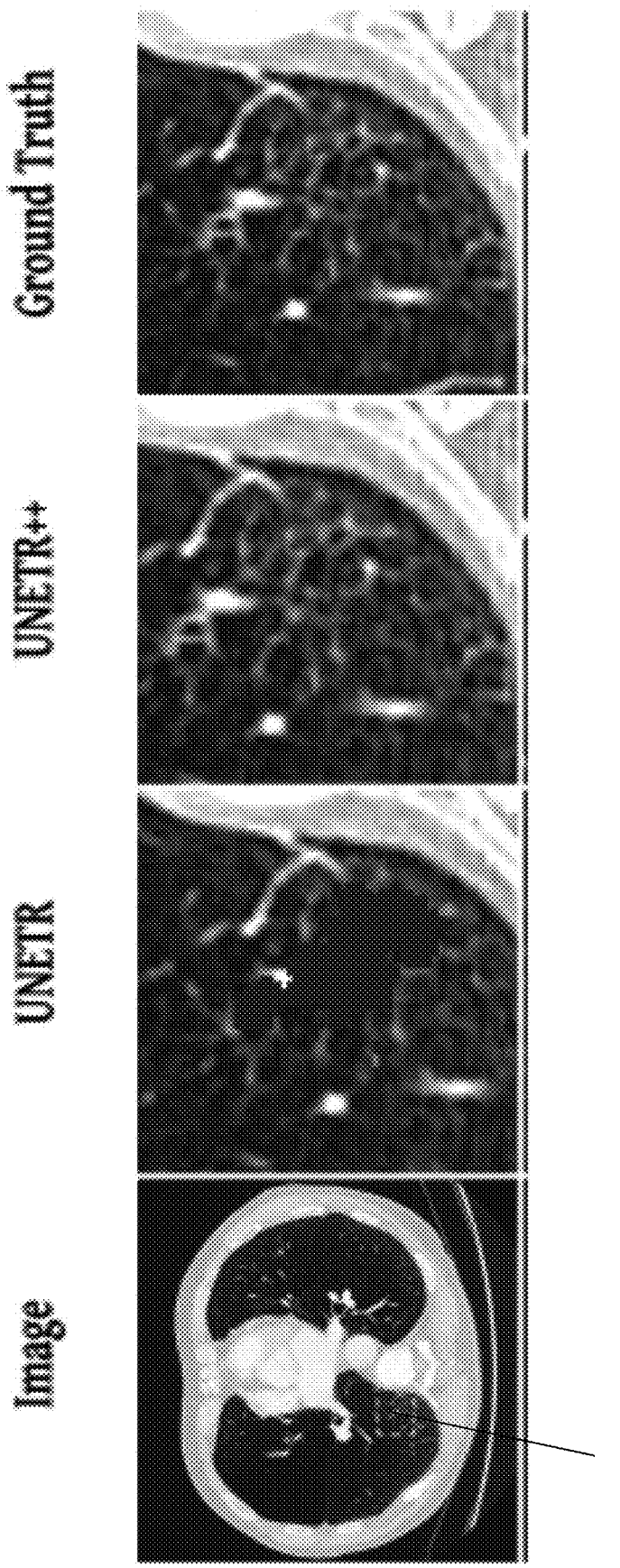
FIGS. 14A-14C illustrate a qualitative comparison between the baseline UNETR and the UNETR++ on Decathlon-Lung dataset.
Figure 14B:
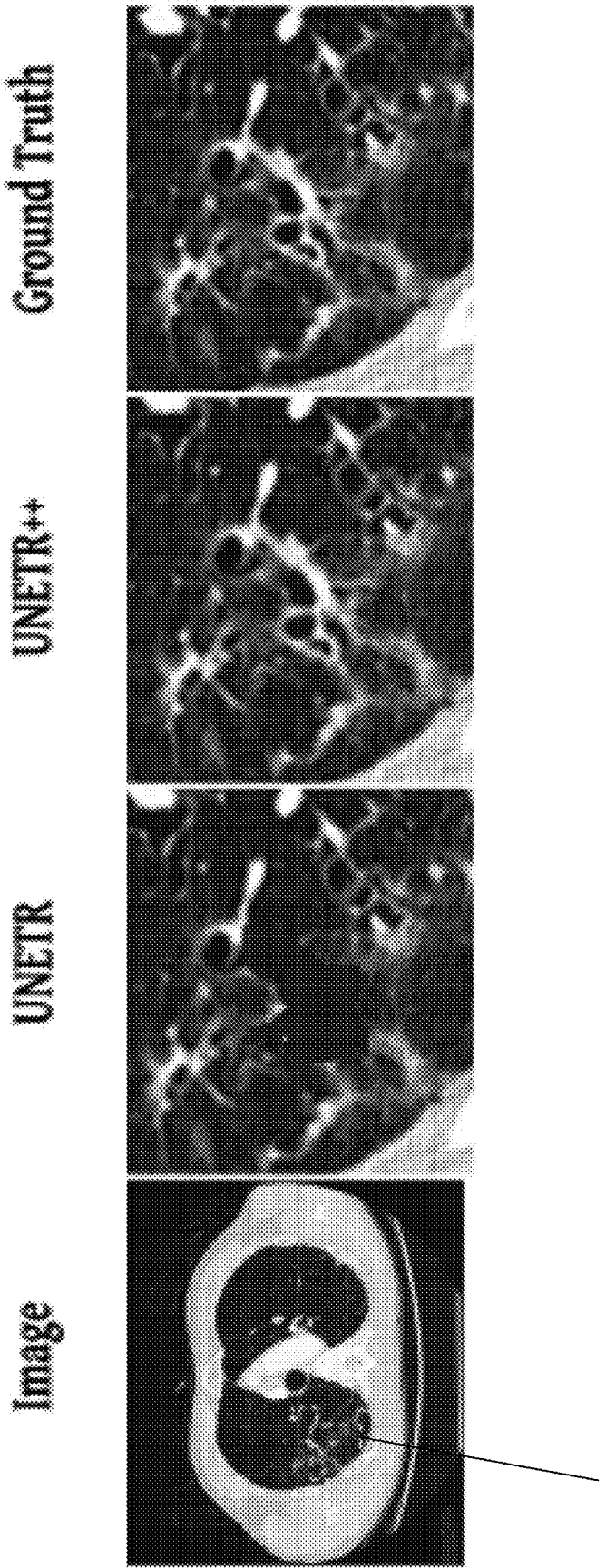
Figure 14C:
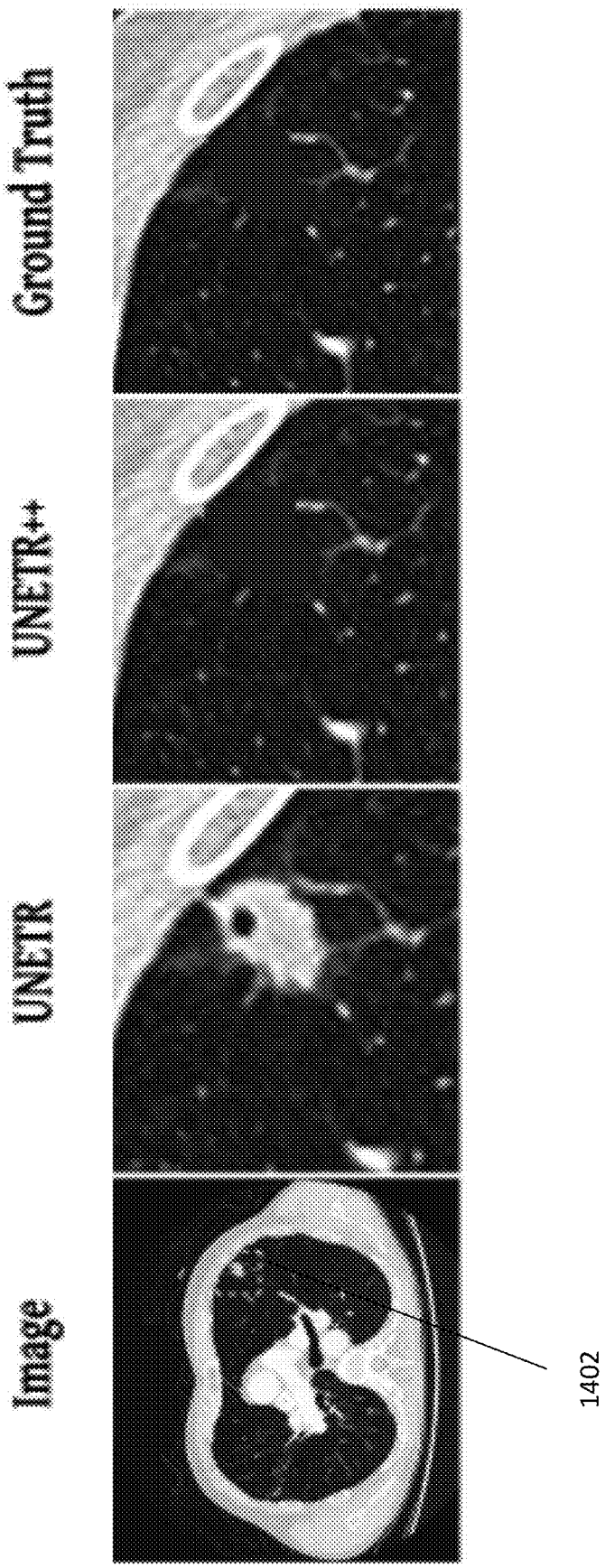

FIGS. 14A, 14B, 14C illustrate a qualitative comparison between the baseline UNETR and the UNETR++ on Decathlon-Lung dataset. The area 1402 is enlarged to demonstrate that UNETR++ has better segmentation and less false positives for segmenting the tumors as compared to UNETR.

Figure 15:
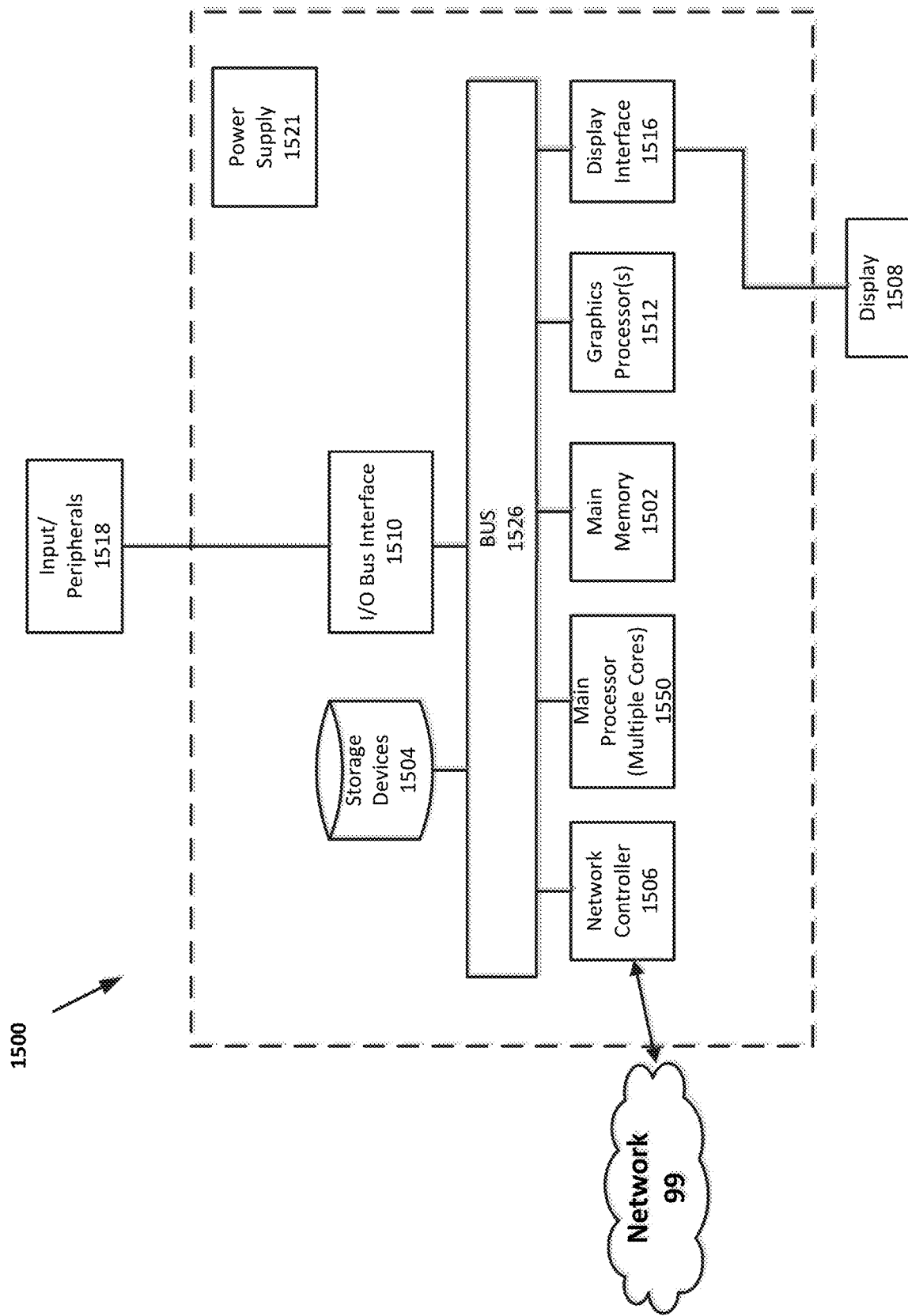
FIG. 15 is a block diagram of a computer system for training a deep learning network.

FIG. 15 is a block diagram illustrating an example computer system for implementing training of the machine learning system and inference methods according to an exemplary aspect of the disclosure. The computer system may be an AI workstation, such as an A100 workstation that was used for training in this disclosure. In some embodiments, the computer system 1500 may include a CPU and a graphics card by NVIDIA, in which the GPUs have multiple CUDA cores. In some embodiments, the computer system 1500 may include a machine learning engine 1512, such as a system on chip by Apple (M2 or greater) or Qualcomm (Snapdragon).

The computer system 1500 is implemented with an operating system, for example Ubuntu Linux OS, Windows Server, a version of Unix OS, or Mac OS Server. The computer system 1500 may include one or more central processing units (CPU) 1550 having multiple cores. The computer system 1500 may include a graphics board 1512 having multiple GPUs, each GPU having GPU memory. The graphics board 1512 may perform many of the mathematical operations of the disclosed machine learning methods. The computer system 1500 includes main memory 1502, typically random access memory RAM, which contains the software being executed by the processing cores 1550 and GPUs 1512, as well as a non-volatile storage device 1504 for storing data and the software programs. Several interfaces for interacting with the computer system 1500 may be provided, including an I/O Bus Interface 1510, Input/Peripherals 1518 such as a keyboard, touch pad, mouse, Display Adapter 1516 and one or more Displays 1508, and a Network Controller 1506 to enable wired or wireless communication through a network 99. The interfaces, memory and processors may communicate over the system bus 1526. The computer system 1500 includes a power supply 1521, which may be a redundant power supply.

Numerous modifications and variations of the present invention are possible in light of the above teachings. It is therefore to be understood that within the scope of the appended claims, the invention may be practiced otherwise than as specifically described herein.

The invention claimed is:

1. A system for 3D medical image segmentation, comprising:
a medical imaging device for obtaining a plurality of 2D images forming a volumetric image;
processing circuitry configured with
a first stage to divide the volumetric image into 3D image patches,
a hierarchical encoder-decoder structure in which resolution of features of the 3D image patches is decreased by a factor of two in each of a plurality of stages of the encoder,
an encoder output connected to the decoder via skip connections, and
a convolutional block to produce a voxel-wise final segmentation mask,
wherein the encoder includes a plurality of efficient paired attention (EPA) blocks each with a spatial attention branch and a channel attention branch that learn respective spatial and channel attention feature maps; and
a display to display the final segmentation mask.

2. The system of claim 1, wherein the medical imaging device is a CT scanning device.

3. The system of claim 1, wherein the medical imaging device is a MRI device.

4. The system of claim 1, wherein the spatial and channel attention modules share weights of queries Q and keys K and have different value layers V.

5. The system of claim 4, wherein each EPA block performs, in parallel, tasks using the spatial and channel attention modules with the shared weights for keys K and the shared weights for queries Q and different value layers V to learn enriched spatial-channel feature representations.

6. The system of claim 1, wherein in each of the EPA blocks,
the spatial attention module aggregates the spatial features by a weighted sum of projected features in a linear manner to compute the spatial attention feature maps; and
the channel attention module determines dependencies in the channels and computes the channel attention feature maps.

7. The system of claim 1, wherein in each of the EPA blocks,
a shared key layer K and a spatial value V layer are projected from a dimension of HWD×C to lower dimensional matrices of shape p×C, where His height, W is width, D is depth, and C is a number of channels, and p is the dimension of a projected vector.

8. The system of claim 7, wherein the processing circuitry is configured to
determine spatial attention maps by multiplying the shared weights of the query Q by a transpose of the projected key K layer followed by a softmax to measure similarity between each feature and the rest of the spatial features; and
determine a final spatial attention feature map by multiplying the measured similarities by the projected spatial value V layer.

9. The system of claim 1, further comprising:
convolutional blocks that receive fused outputs of the spatial and channel attention modules to enhance the feature maps.

10. The system of claim 1, wherein each of a plurality of stages of the decoder consist of an upsampling layer using deconvolution to increase the resolution of the feature maps by a factor of two, followed by the EPA block.

11. A method of 3D medical image segmentation, comprising:
obtaining, by a medical imaging device, a plurality of 2D images forming a volumetric image;
dividing, by a first circuitry stage, the volumetric image into 3D image patches;
decreasing, in a hierarchical encoder structure, resolution of features of the 3D image patches by a factor of two in each of a plurality of stages of an encoder;
transmitting an output of the encoder to a hierarchical decoder via skip connections;
learning, with spatial and channel attention branches in a plurality of efficient paired attention (EPA) blocks, spatial and channel attention feature maps; and
producing, by a convolutional block, a voxel-wise final segmentation mask;
and
displaying on a display the final segmentation mask.

12. The method of claim 11, further comprising sharing between the spatial and channel attention modules weights of queries Q and keys K.

13. The method of claim 12, further comprising:
performing, by each EPA block in parallel, tasks using the spatial and channel attention modules with the shared weights for keys K and the shared weights for queries Q and different value layers V to learn enriched spatial-channel feature representations.

14. The method of claim 11, further comprising:
aggregating, by the spatial attention module, the spatial features by a weighted sum of projected features in a linear manner to compute the spatial attention feature maps; and
determining, by the channel attention module, dependencies in the channels and computing the channel attention feature maps.

15. The method of claim 11, further comprising:
projecting a shared key layer K and a spatial value V layer from a dimension of HWD×C to lower dimensional matrices of shape p×C, where H is height, W is width, D is depth, and C is a number of channels, and p is the dimension of a projected vector.

16. The method of claim 15,
determining spatial attention maps by multiplying the shared weights for the query Q by a transpose of the projected key K layer followed by a softmax to measure similarity between each feature and the rest of the spatial features; and
determining a final spatial attention feature map by multiplying the measured similarities by the projected spatial value V layer.

17. The method of claim 11, further comprising:
receiving, by convolutional blocks, fused outputs of the spatial and channel attention modules to enhance the feature maps.

18. The method of claim 11, further comprising:
using deconvolution, by an upsampling layer, before the EPA block, in each of a plurality of stages of the decoder, to increase the resolution of feature maps by a factor of two.

19. A non-transitory computer readable storage medium storing program instructions, which when executed by processing circuitry perform a method comprising:
obtaining a plurality of 2D images forming a volumetric image;
dividing, by a first stage, the volumetric image into 3D image patches;
decreasing, in a hierarchical encoder structure, resolution of features of the 3D image patches by a factor of two in each of a plurality of stages of the encoder;
transmitting an output of the encoder to a hierarchical decoder via skip connections;
learning, with spatial and channel attention branches in a plurality of efficient paired attention (EPA) blocks, spatial and channel attention feature maps;
producing, by a convolutional block, a voxel-wise final segmentation mask; and
displaying on a display the final segmentation mask.

20. The storage medium of claim 19, further comprising:
projecting a shared key layer K and a spatial value V layer from a dimension of HWD×C to lower dimensional matrices of shape p×C, where H is height, W is width, D is depth, and C is a number of channels, and p is the dimension of a projected vector.

* * * * *